United States Patent
Saito et al.

(10) Patent No.: US 8,178,102 B2
(45) Date of Patent: May 15, 2012

(54) EMULSIFIED COMPOSITION FOR DILUTION AND CANCER VACCINE COMPOSITION

(75) Inventors: Koichi Saito, Ibaraki (JP); Yusuke Okawa, Kawasaki (JP)

(73) Assignees: Dainippon Sumitomo Pharma Co., Ltd., Osaka-shi (JP); NOF Corporation, Tokyo (JP)

( * ) Notice: Subject to any disclaimer, the term of this patent is extended or adjusted under 35 U.S.C. 154(b) by 1167 days.

(21) Appl. No.: 11/814,270

(22) PCT Filed: Jan. 19, 2006

(86) PCT No.: PCT/JP2006/301171
§ 371 (c)(1),
(2), (4) Date: Sep. 20, 2007

(87) PCT Pub. No.: WO2006/078059
PCT Pub. Date: Jul. 27, 2006

(65) Prior Publication Data
US 2009/0136572 A1      May 28, 2009

(30) Foreign Application Priority Data
Jan. 19, 2005   (JP) ................................ 2005-012140

(51) Int. Cl.
*A61K 39/39*   (2006.01)
*B01F 3/08*    (2006.01)

(52) U.S. Cl. ........... 424/184.1; 516/20; 516/21; 516/27; 516/28; 516/29; 516/30

(58) Field of Classification Search ............ 516/20, 516/21, 27, 28, 29, 30; 424/184.1
See application file for complete search history.

(56) References Cited

U.S. PATENT DOCUMENTS

| | | | |
|---|---|---|---|
| 5,444,041 A * | 8/1995 | Owen et al. .................. 514/2 |
| 5,744,137 A | 4/1998 | Stone | |
| 5,814,321 A | 9/1998 | Miyahara et al. | |
| 6,235,282 B1 * | 5/2001 | Riviere et al. .............. 424/184.1 |
| 6,458,363 B1 | 10/2002 | Schrier et al. | |
| 2005/0158330 A1 | 7/2005 | Saito et al. | |
| 2007/0036808 A1 | 2/2007 | Sugiyama | |
| 2008/0187552 A1 | 8/2008 | Aucouturier et al. | |

FOREIGN PATENT DOCUMENTS

| | | |
|---|---|---|
| EP | 1 095 662 A1 | 5/2001 |
| EP | 1 097 721 A2 | 5/2001 |
| JP | 07-509733 A | 10/1995 |
| JP | 09-268130 A | 10/1997 |
| JP | 10-158152 A | 6/1998 |
| JP | 2001-131087 A | 5/2001 |
| WO | 94/20071 A1 | 9/1994 |
| WO | 96/24374 A1 | 8/1996 |
| WO | 99/53947 A1 | 10/1999 |
| WO | 00/37101 A1 | 6/2000 |
| WO | 2004/024175 A1 | 3/2004 |
| WO | 2004/060396 A2 | 7/2004 |

OTHER PUBLICATIONS

Murdan, S., et al., J. Pharm. Sci., 88(6): 615-619, 1999.*
Rosenberg et al., *Immunity*, 10: 281-287 (Mar. 1999).
Wang et al., *Clinical Cancer Research*, 5: 2756-2765 (Oct. 1999).
Aucouturier et al., *Expert. Rev. Vaccines*, 1(1): 111-118 (2002).
Japanese Patent Office, Office Action in Japanese Patent Application No. 554007/2006 (Jul. 26, 2011).
Japanese Patent Office, Notice of Reasons for Refusal in Japanese Patent Application No. 554007/2006 (Mar. 21, 2012).

\* cited by examiner

*Primary Examiner* — Alana Harris Dent
*Assistant Examiner* — Anne Holleran
(74) *Attorney, Agent, or Firm* — Leydig, Voit & Mayer, Ltd.

(57) ABSTRACT

Provided is an emulsified composition for diluting a cancer antigen peptide or a dimer thereof. Also provided is a novel cancer vaccine composition or specific CTL inducer that efficiently induces CTL irrespective of the type of cancer antigen peptide when mixing the emulsified composition for dilution and a water phase comprising a cancer antigen peptide or a dimer thereof.

The present invention relates to an emulsified composition for diluting a cancer antigen peptide or a dimer thereof, comprising a particular ester, a particular surfactant, a particular emulsifier, and a water phase. The present invention also relates to a cancer vaccine composition or specific CTL inducer obtained by freshly diluting and mixing a water phase comprising a cancer antigen peptide or a dimer thereof with the emulsified composition for dilution.

20 Claims, 5 Drawing Sheets

EMULSIFIED COMPOSITION FOR DILUTION AND CANCER VACCINE COMPOSITION

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: 8,318 bytes ASCII (Text) file named "701720ReplacementSequenceListing.txt," created Oct. 9, 2008.

TECHNICAL FIELD

The present invention belongs to the field of cancer immunotherapy and relates to an emulsified composition for diluting a cancer antigen peptide or a diner thereof, having cytotoxic T cell induction activity. More specifically, the present invention relates to an emulsified composition for diluting a cancer antigen peptide or a dimer thereof, comprising a particular ester, a surfactant, an emulsifier, and a water phase, and occurring in the form of a stable W/O emulsion. The present invention also relates to a cancer vaccine composition or specific cytotoxic T cell inducer, comprising a particular ester, a surfactant, an emulsifier, and a water phase comprising a cancer antigen peptide consisting of a particular amino acid sequence or a dimer thereof, and occurring in the form of a stable W/O emulsion.

BACKGROUND ART

In the elimination of cancer cells, virus-infected cells and the like by the living body, cellular immunity, particularly cytotoxic T cells (hereinafter referred to as CTL) play an important role. CTL recognizes the complex formed on cancer cells by a cancer antigen protein-derived antigen peptide (cancer antigen peptide) and MHC (Major Histocompatibility Complex) class I antigen (in the case of humans, referred to as HLA antigen), and attacks/destroys the cancer cells.

As a representative example of the cancer antigen protein, those described in the table of Immunity, Vol. 10, page 281, 1999 can be mentioned. Specifically, gp100 and MART-1, which are melanocyte tissue specific proteins, and melanosome proteins such as tyrosinase can be mentioned. As the cancer antigen protein other than melanoma, cancer markers such as CEA, PSA, and HER2/neu can be mentioned. TERT, whose expression increases in cancer, and the like can also be mentioned. Furthermore, WT1, which is highly expressed in many types of cancer, is also known as a novel cancer antigen protein in leukemia and solid cancers.

The cancer antigen peptide is a peptide resulting from processing of a cancer antigen protein by intracellular protease. As stated above, a complex of this resulting cancer antigen peptide and MHC class I antigen (HLA antigen) is presented to the cell surface and recognized by CTL. However, in developing a cancer immunotherapeutic agent (cancer vaccine) utilizing cancer cell destruction by CTL, it has been difficult to efficiently induce CTL using a cancer antigen peptide alone, because of the generally low immunogenicity. Therefore, there is a demand for the development of a preparation capable of stimulating CTL induction.

To this end, many investigations have been conducted regarding preparations that stimulate CTL induction. Particularly, many investigations have been conducted regarding emulsion type preparations.

Generally, there are different types of emulsion preparations: O/W emulsions and W/O emulsions.

In the case of O/W emulsions, the peptide that serves as the antigen cannot be retained in the inner phase, and therapeutically effective specific CTL induction activity is not exhibited.

In the case of W/O emulsions, in which the water phase serves as the inner phase, excellent CTL induction activity is expected because the peptide that serves as the antigen is easy to retain in the inner phase, but there are many problems to be solved before they are brought into practical applications.

For example, as a W/O emulsion for cancer antigen peptide carrier, incomplete Freund's adjuvant is known, but effective activity cannot be obtained in some cases due to insufficient stability. There have been other problems such as difficulty in administration due to high viscosity.

Incomplete Freund's adjuvant has long been known as an immunopotentiating adjuvant that causes inactivated bacteria or inactivated virus to be included to induce antibody production, and alternative W/O emulsion type vaccine compositions were investigated; for example, the compositions described in Japanese Patent Kohyo publication No. HEI-7-509733, the pamphlet for International Patent Publication No. 94/20071, and Japanese Patent Kokai Publication No. HEI-9-268130 were proposed.

As a substitute for incomplete Freund's adjuvant, an application of W/O/W composite emulsion to vaccine is proposed in Japanese Patent Kokai Publication No. 2001-131087.

However, as a cancer antigen peptide carrier to substitute for incomplete Freund's adjuvant, no W/O emulsion capable of therapeutically effectively activating CTL induction is known.

Generally, because cancer antigen peptides are low-molecular compounds, it is not easy to keep them stable in W/O emulsion. Furthermore, it is feared that the cancer antigen peptide undergoes degradation, aggregation and the like due to the energy during emulsification. Furthermore, cancer antigen peptides range from highly water-soluble ones to slightly soluble ones depending on the amino acid sequence thereof. Therefore, there is a demand for the development of a cancer vaccine based on a highly versatile W/O emulsion that therapeutically effectively stimulates CTL induction, irrespective of the properties of the cancer antigen peptide.

An object of the present invention is to provide an emulsified composition for dilution for preparing a cancer vaccine composition that exhibits effective CTL induction activity in vivo in various cancer antigen peptides, and is of low viscosity and excellent stability. Another object of the present invention is to provide a method of preparing a novel cancer vaccine that specifically stimulates CTL induction in vivo according to the cancer antigen peptide contained, using the above-described emulsified composition for dilution, and the composition.

DISCLOSURE OF THE INVENTION

The present inventors found that by diluting various peptides known as cancer antigens with a particular emulsified composition comprising a particular ester and a particular surfactant, CTL induction activity specific for each antigen can be exhibited, irrespective of the type and properties of the peptide, conducted further diligent investigations, and completed the present invention.

Accordingly, the present invention encompasses the following modes of embodiment:

[1] An emulsified composition for diluting a cancer antigen peptide having 8 to 12 amino acids or a dimer thereof, comprising:
A) an ester of a fatty acid having 8 to 22 carbon atoms and an alcohol having 2 to 24 carbon atoms, the ester having a solidification point of not more than 10° C., at 50 to 90% by weight;
B) a nonionic surfactant consisting of a hydroxy fatty acid triglyceride adduct with 5 to 20 mol of ethylene oxide, at 0.5 to 20% by weight;
D) water at 5 to 20% by weight.

[2] An emulsified composition for diluting a cancer antigen peptide having 8 to 12 amino acids or a dimer thereof, comprising:
A) an ester of a fatty acid having 8 to 22 carbon atoms and an alcohol having 2 to 24 carbon atoms, the ester having a solidification point of not more than 10° C., at 50 to 90% by weight;
B) a nonionic surfactant consisting of a hydroxy fatty acid triglyceride adduct with 5 to 20 mol of ethylene oxide, at 0.5 to 20% by weight;
C) an emulsifier that is a partial ester of a polyhydric alcohol and a fatty acid, the partial ester being liquid at 40° C., at 0 to 20% by weight; and
D) water at 5 to 20% by weight.

[3] The emulsified composition for dilution described in [2], comprising:
ingredient A at 60 to 80% by weight;
ingredient B at 1 to 10% by weight;
ingredient C at 5 to 15% by weight; and
ingredient D at 5 to 20% by weight.

[4] The emulsified composition for dilution described in any of [1] to [3], wherein the average particle diameter of the dispersion phase of the emulsified composition for dilution is 50 to 500 nm.

[5] The emulsified composition for dilution described in any of [1] to [4], wherein the fatty acid that constitutes ingredient A is oleic acid, myristic acid or 2-ethylhexanoic acid.

[6] The emulsified composition for dilution described in any of [1] to [5], wherein the ester of ingredient A is ethyl oleate, octyldodecyl myristate or cetyl 2-ethylhexanoate.

[7] The emulsified composition for dilution described in any of [1] to [6], wherein the hydroxy fatty acid triglyceride that constitutes the ingredient B nonionic surfactant is castor oil or hardened castor oil.

[8] A method of preparing a cancer vaccine composition, comprising diluting 0.25 to 1 part by volume of a water phase comprising a cancer antigen peptide having 8 to 12 amino acids or a dimer thereof with 1 part by volume of the emulsified composition for dilution described in any of [1] to [7].

[9] A cancer vaccine composition comprising:
A) an ester of a fatty acid having 8 to 22 carbon atoms and an alcohol having 2 to 24 carbon atoms, the solidification point of the ester being not more than 10° C., at 30 to 80% by weight;
B) a nonionic surfactant consisting of a hydroxy fatty acid triglyceride adduct with 5 to 20 mol of ethylene oxide, at 0.5 to 20% by weight;
C) an emulsifier that is a partial ester of a polyhydric alcohol and a fatty acid, the partial ester being liquid at 40° C., at 0 to 20% by weight; and
E) a water phase comprising a cancer antigen peptide having 8 to 12 amino acids or a dimer thereof, at 10 to 60% by weight;
wherein the composition is a W/O emulsion.

[10] The cancer vaccine composition described in [9], comprising
ingredient A at 40 to 60% by weight;
ingredient B at 1.0 to 5.0% by weight;
ingredient C at 5.0 to 10.0% by weight; and
ingredient E at 30 to 50% by weight.

[11] A specific CTL inducer comprising:
A) an ester of a fatty acid having 8 to 22 carbon atoms and an alcohol having 2 to 24 carbon atoms, the solidification point of the ester being not more than 10° C., at 30 to 80% by weight;
B) a nonionic surfactant consisting of a hydroxy fatty acid triglyceride adduct with 5 to 20 mol of ethylene oxide, at 0.5 to 20% by weight;
C) an emulsifier that is a partial ester of a polyhydric alcohol and a fatty acid, the partial ester being liquid at 40° C., at 0 to 20% by weight; and
E) a water phase comprising a cancer antigen peptide having 8 to 12 amino acids or a dimer thereof, at 10 to 60% by weight;
wherein the composition is a W/O emulsion.

[12] The specific CTL inducer described in [11], comprising
ingredient A at 40 to 60% by weight;
ingredient B at 1.0 to 5.0% by weight;
ingredient C at 5.0 to 10.0% by weight; and
ingredient E at 30 to 50% by weight.

[13] A kit for freshly preparing a cancer vaccine composition or specific CTL inducer, comprising a water phase comprising a cancer antigen peptide having 8 to 12 amino acids or a dimer thereof, and the emulsified composition for dilution for diluting the water phase, described in any of [1] to [7].

[14] A commercial package comprising a water phase comprising a cancer antigen peptide having 8 to 12 amino acids or a dimer thereof, the emulsified composition for dilution described in any of [1] to [7], and a printed matter bearing the statement that a W/O emulsion obtained by diluting the water phase with an emulsified composition for dilution can be used, or should be used, for the treatment or prevention of cancer.

BEST MODE FOR EMBODYING THE INVENTION

Figure 1:
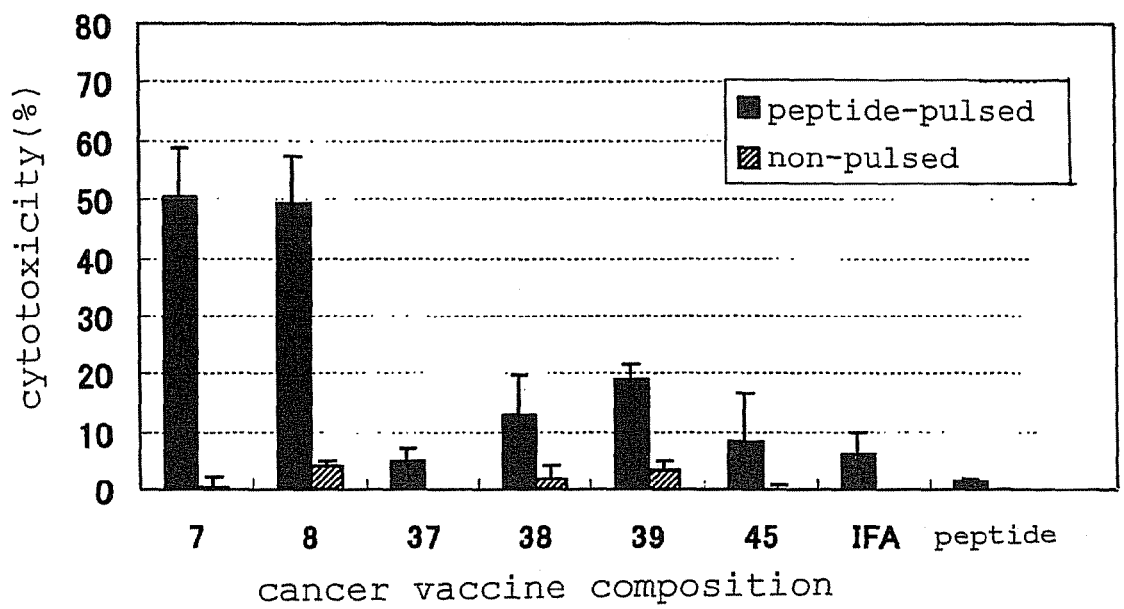
FIG. 1 is a graph showing the results of specific CTL induction using cancer vaccine compositions comprising the TERT peptide.

The emulsified composition for dilution of the present invention is hereinafter described in detail.

The "emulsified composition for dilution" of the present invention refers to a composition used to dilute a cancer antigen peptide or a dimer thereof. The "cancer vaccine composition" of the present invention refers to a composition obtained by diluting a cancer antigen peptide or a dimer thereof with the emulsified composition for dilution of the present invention.

The emulsified composition for dilution of the present invention is an emulsion pre-emulsified into the w/o type. The emulsified composition for dilution of the present invention is a composition for diluting a water phase comprising a cancer antigen peptide having 8 to 12 amino acids or a dimer thereof; by so diluting the water phase, a cancer vaccine composition that stimulates CTL induction specific for each cancer antigen peptide can be prepared.

In the emulsified composition for dilution of the present invention, ingredient A is an ester of a fatty acid and an alcohol, preferably an ester of a fatty acid having 8 to 22 carbon atoms and an alcohol having 2 to 24 carbon atoms, the solidification point of the ester being not more than 10° C.

The ester of a fatty acid and an alcohol, used as ingredient A, may be chosen from among those that have a solidification point of not more than 10° C. If the solidification point of ingredient A exceeds 10° C., it is feared that the stability, particularly the stability at low temperature, of the emulsified composition for dilution decreases, and this is therefore undesirable.

As examples of the fatty acid having 8 to 22 carbon atoms, saturated or unsaturated fatty acids having 8 to 22 carbon atoms can be mentioned; specifically, caprylic acid, 2-ethylhexanoic acid, nonanoic acid, capric acid, undecanoic acid, lauric acid, tridecanoic acid, myristic acid, myristoleic acid, pentadecanoic acid, palmitic acid, isopalmitic acid, palmitoleic acid, isostearic acid, stearic acid, oleic acid, linoleic acid and the like can be mentioned. As examples of the alcohol having 2 to 24 carbon atoms, alkanols having 2 to 24 carbon atoms and alkenols having 2 to 24 carbon atoms can be mentioned; specifically, alcohols such as ethanol, propanol, isopropanol, ethylene glycol, butanol, hexanol, octanol, 2-ethylhexanol, decanol, dodecanol, myristyl alcohol, cetyl alcohol, isocetyl alcohol (2-hexyldecanol), isostearyl alcohol, oleyl alcohol, icosenol, docosenol, tetracosenol, and 2-octyldodecanol and the like can be mentioned.

As examples of the ingredient A used in the present invention, specifically, cetyl 2-ethylhexanoate, hexyl laurate, butyl myristate, isopropyl myristate, isocetyl myristate, octyldodecyl myristate, 2-ethylhexyl palmitate, isostearyl palmitate, isopropyl isostearate, isocetyl isostearate, 2-ethylhexyl stearate, ethyl oleate, decyl oleate, oleyl oleate, octyldodecyl oleate, ethyl linoleate, isopropyl linoleate and the like can be mentioned.

The ingredient A used in the present invention may be synthesized as an ester, and may be extracted/purified from a natural oil or fat. As examples of the naturally derived ester oil, jojoba oil, orange roughy oil and the like can be mentioned. These esters are generally commercially available, from among which one suitable for pharmaceutical use may be chosen according to the purpose.

The ingredient A used in the present invention is preferably an oleic acid ester, a myristic acid ester or a 2-ethylhexanoeic acid ester, more preferably ethyl oleate, octyldodecyl myristate, or cetyl 2-ethylhexanoate, still more preferably ethyl oleate.

In the emulsified composition for dilution of the present invention, the content of ingredient A is 50 to 90% by weight, preferably 55 to 85% by weight, more preferably 60 to 80% by weight. If the content of ingredient A is less than 50% by weight, the finished cancer vaccine composition obtained by diluting a cancer antigen peptide possibly becomes unstable, and this is therefore undesirable.

In the emulsified composition for dilution of the present invention, the ingredient B is a nonionic surfactant consisting of a hydroxy fatty acid triglyceride adduct with 5 to 20 mol of ethylene oxide.

The hydroxy fatty acid triglyceride adduct with ethylene oxide is a surfactant widely used for emulsification, solubilization and the like, and 5 to 100 mol of ethylene oxide adducts are commercially available. A surfactant consisting of less than 5 mol of ethylene oxide adduct has a low surfactant activity such that an emulsified composition for dilution showing a good emulsified state cannot be formed, and this is therefore undesirable. Because a surfactant consisting of more than 20 mol of ethylene oxide adduct is highly hydrophilic, not only it is feared that the emulsification stability decreases due to aggregation of water phase particles and the like in the cancer vaccine composition obtained by diluting the emulsified composition, but also the CTL induction activity for the cancer vaccine composition can decrease, and this is therefore undesirable.

The nonionic surfactant used as the ingredient B is preferably constituted by a castor oil or hardened castor oil adduct with 5 to 20 mol of ethylene oxide. By using such a nonionic surfactant, an emulsified composition for dilution of excellent stability can be obtained, and, furthermore, a cancer vaccine composition that exhibits excellent stability and high CTL induction activity when a cancer antigen peptide is diluted with the emulsified composition for dilution can be prepared. By using a nonionic surfactant constituted by a castor oil or hardened castor oil adduct with 5 to 20 mol of ethylene oxide, a cancer vaccine composition of excellent safety to the administration site can be finally prepared. Of these, preferable as the ingredient B of the present invention is a hardened castor oil adduct with 10 to 20 mol of ethylene oxide. Furthermore, in the present invention, it is most preferable to use, out of these, a hardened castor oil adduct with 10 mol of ethylene oxide.

In the emulsified composition for dilution of the present invention, the content of ingredient B is 0.5 to 20% by weight, preferably 1 to 15% by weight, more preferably 1 to 10% by weight. If the content of ingredient B is less than 0.5% by weight, the surfactant activity decreases in excess and, as a result, it is possible that no stable emulsified composition for dilution is obtained, and this is therefore undesirable. Conversely, if the content exceeds 20% by weight, not only phase conversion occurs during dilution of the cancer antigen peptide, which hampers the final obtainment of a good cancer vaccine composition, but also it is feared that the safety of the cancer vaccine composition to the administration site decreases, and this is therefore again undesirable.

The ingredient C optionally contained in the emulsified composition for dilution of the present invention is an emulsifier that is a partial ester of a polyhydric alcohol and a fatty acid, the partial ester being liquid at 40° C.

In the present invention, in addition to the above-described ingredient B, by containing ingredient C, a cancer vaccine composition that exhibits a better emulsified state and has excellent stability when used to dilute a cancer antigen peptide can be prepared and, as a result, a cancer vaccine composition that exhibits excellent CTL induction activity in diversified kinds of peptides can be obtained.

As examples of the polyhydric alcohol that constitutes the ingredient C of the present invention, glycerin, diglycerin, sorbitan, sorbitol, sorbide, mannitan, mannitol, sucrose and the like can be mentioned. As examples of the fatty acid that constitutes the ingredient C, lauric acid, myristic acid, isostearic acid, oleic acid, linoleic acid and the like can be mentioned. As the ingredient C of the present invention, one being liquid at 40° C. may be chosen from among these partial esters of a polyhydric alcohol and a fatty acid.

As specific suitable examples of ingredient C, glycerin monooleate, glycerin dioleate, diglycerin monooleate, diglycerin dioleate, sorbitan monooleate, sorbitan sesquioleate, sorbitan dioleate, sorbitan trioleate, mixtures thereof and the like can be mentioned. Particularly suitable ones are glycerin monooleate, glycerin dioleate, sorbitan monooleate, sorbitan sesquioleate, sorbitan dioleate, and mixtures thereof. These are generally commercially available, from among which those suitable for pharmaceutical use can be chosen.

In the emulsified composition for dilution of the present invention, the content of ingredient C is chosen from the range of 0 to 20% by weight. In particular, the range of 1 to 20% by weight is preferable, and the range of 5 to 15% by weight is more preferable. At this time, if the content exceeds 20% by weight, not only the viscosity for the emulsified composition for dilution increases so that a good cancer vaccine composition cannot be obtained when the cancer antigen peptide of the present invention is diluted, but also it is feared that the safety of the cancer vaccine composition to the administration site decreases, and this is therefore undesirable. If the content of ingredient C is not less than 1% by weight, a sufficient additive effect is exhibited, and this is therefore preferable.

The ingredient D that constitutes the emulsified composition for dilution of the present invention is a water phase for forming an emulsion. The ingredient D of the present invention may be chosen from among aqueous ingredients in common use in pharmaceuticals; for example, purified water, water for injection, phosphate-buffered solution, physiological saline, phosphate-buffered saline and the like can be mentioned. The content of ingredient D in the emulsified composition for dilution of the present invention is 5 to 20% by weight, preferably 8 to 16% by weight.

In the emulsified composition for dilution of the present invention, in addition to the above-described ingredients, an antioxidant, a stabilizer and the like can also be added, as long as the emulsion stability is not affected.

As examples of the antioxidant, tocopherols such as α-tocopherol and δ-tocopherol, gallic acid esters, dibutylhydroxytoluene and the like can be mentioned.

As the stabilizer, alcohols such as glycerin, propylene glycol, 1,3-butylene glycol, polyethylene glycol and the like can be mentioned.

The emulsified composition for dilution of the present invention can be produced by an ordinary method of producing an emulsified composition adopted as appropriate. Usually, a method is chosen in which ingredient A, ingredient B and ingredient C are previously mixed, ingredient D is gradually added while stirring the mixture, and the mixture is finally stirred and emulsified using an emulsifying apparatus such as a homogenizer.

The emulsified composition for dilution of the present invention is preferably obtained in the form of a W/O emulsion having a very low viscosity and a fine particle diameter.

The average particle diameter of the dispersion phase of the emulsified composition for dilution of the present invention is preferably not more than 1000 nm, more preferably not more than 500 nm, still more preferably 50 to 500 nm, particularly preferably 50 to 300 nm.

In the present invention, the average particle diameter of the dispersion phase of the emulsified composition for dilution is expressed as the mean of the particle diameters of all particles (dispersion phase) measured by the dynamic light scattering method. Specifically, particle diameters can be measured by applying a sample obtained by diluting as appropriate an emulsified composition as the subject of measurement with ingredient A to, for example, ZETASIZER NANO-S manufactured by MALVERN INSTRUMENTS Company and the like.

If the average particle diameter of the dispersion phase exceeds 1000 nm, not only the stability for the emulsified composition for dilution decreases, but also it is feared that the homogeneity, stability, and CTL induction activity of the cancer vaccine composition finally obtained by diluting a water phase comprising a cancer antigen peptide decrease, and this is therefore undesirable. Provided that the average particle diameter of the dispersion phase is 50 to 300 nm, the emulsified composition can also be filter-sterilized in the state of a W/O emulsion. The filter used for the filter sterilization may be chosen as appropriate to the filtration of oily liquid. Specifically, a hydrophobic membrane filter having a pore diameter of 0.2 μm (made of polytetrafluoroethylene) and the like can be mentioned.

The emulsified composition for dilution of the present invention is used to obtain a cancer vaccine or specific CTL inducer that stimulates CTL induction specific for each antigen when combined with a cancer antigen peptide having 8 to 12 amino acids or a dimer thereof. In so preparing a cancer vaccine composition or specific CTL inducer, 0.25 to 1 part by volume of a water phase comprising a cancer antigen peptide having 8 to 12 amino acids or a dimer thereof may be diluted with 1 part by volume of an emulsified composition for dilution. At this time, the cancer antigen peptide or dimer thereof may be dissolved or suspended in the water phase.

The emulsified composition for dilution of the present invention is a W/O emulsion having water particles finely dispersed therein, and is of very low viscosity. Therefore, when a peptide-containing water phase is diluted with this emulsified composition for dilution, a stable W/O emulsion can be easily obtained. The emulsified composition of the present invention is a stable W/O emulsion per se. The cancer vaccine composition or specific CTL inducer obtained by diluting a water phase comprising a cancer antigen peptide with the emulsified composition of the present invention as described above is also a stable W/O emulsion.

Therefore, as the stirring methods for diluting a water phase comprising a cancer antigen peptide with the emulsified composition for dilution of the present invention, an ordinary emulsifying apparatus such as a homogenizer or homomixer may be used, and a simple stirring apparatus not in common use for emulsification, for example, a shikenkan mixer and the like may be used. The above-described dilution can also be performed by the syringe connection method, which permits simple operation in the laboratory. Hence, the dilution can also be freshly prepared just before administration according to the intended use.

Preferably, by adding an emulsified composition for dilution and a water phase comprising a cancer antigen peptide or a dimer thereof in a ratio by volume of 1:0.25 to 1:1, and then stirring the mixture using a shikenkan mixer for about 30 seconds to 3 minutes according to stirring speed, a stable and good cancer vaccine composition or specific CTL inducer can be obtained. At this time, it is preferable that while the emulsified composition for dilution is stirred using the shikenkan mixer, the water phase comprising the cancer antigen peptide is gradually added, and after the entire quantity to be added has been added, the mixture is further stirred for not less than 30 seconds.

The cancer vaccine composition or specific CTL inducer in the present invention is obtained by diluting and mixing a water phase comprising a cancer antigen peptide having 8 to 12 amino acids or a dimer thereof with the emulsified composition for dilution of the present invention as described above, and, as described above, occurs in the form of a stable W/O emulsion.

Peptides are generally susceptible to heat, and are often difficult to keep stable in water for a long time. As described above, in the present invention, because the dilution can be prepared before use by a simple method, even when using a peptide of relatively low stability to heat and in water, the degradation and aggregation of the peptide during emulsifying operation and storage are reduced. Hence, because undesirable deterioration of a cancer antigen peptide having 8 to 12 amino acids or a dimer thereof is avoided by using the emulsified composition for dilution of the present invention, it becomes possible to prepare a cancer vaccine composition or specific CTL inducer that stably retains various peptides (including dimers thereof), irrespective of the kind and properties thereof.

In the present invention, the cancer antigen peptide is a cancer antigen peptide having 8 to 12 amino acids or a dimer thereof, presented to MHC class I antigen, and comprising a peptide recognized as an antigen by CTL.

In the present invention, the cancer antigen peptide having 8 to 12 amino acids can be chosen from among commonly known ones. For example, partial peptides derived from gp100 and MART-1, which are melanocyte tissue specific proteins, and melanosome proteins such as tyrosinase, can be mentioned. As other cancer antigen peptides, partial peptides derived from cancer markers such as CEA, PSA, and HER2/neu; partial peptides derived from cancer-testis antigens such as MAGE-1, MAGE-2, MAGE-3 and NY-ESO-1; partial peptides derived from epithelial cancer cell protein such as MUC-1, SART-1, and SART-3, and the like can be mentioned. Furthermore, partial peptides derived from TERT, whose expression is increased in cancer, WT1-derived partial peptides, Survivin-2B-derived partial peptides and the like can also be mentioned as suitable cancer antigen peptides.

These may be natural substances or modifications thereof wherein some amino acids have been modified, as long as they do not interfere with therapeutically effective specific CTL induction for each cancer antigen in the finally obtained cancer vaccine composition or specific CTL inducer.

These cancer antigen peptides may be contained in the cancer vaccine composition or specific CTL inducer not only singly, but also in combination of two or more kinds.

These cancer antigen peptides can be obtained by solid phase synthesis based on the Fmox method and the like, and other commonly known methods.

As specific examples of the amino acid sequence of each cancer antigen peptide, the following can be mentioned. Cancer antigen peptides having the amino acid sequences shown below are commonly known.

(1) For gp100-derived peptides, KTWGQYWQV (SEQ ID NO:1), AMLGTHTMEV (SEQ ID NO:2), MLGTHT- MEV (SEQ ID NO:3), ITDQVPFSV (SEQ ID NO:4), YLEPGPVTA (SEQ ID NO:5), LLDGTATLRL (SEQ ID NO:6), VLYRYGSFSV (SEQ ID NO:7), SLADTNSLAV (SEQ ID NO:8), RLMKQDFSV (SEQ ID NO:9), RLPRIFCSC (SEQ ID NO:10), VYFFLPDHL (SEQ ID NO:11) and the like;

(2) for MART-1-derived peptides, AAGIGILTV (SEQ ID NO:12), EAAGIGILTV (SEQ ID NO:13), ILTVILGVL (SEQ ID NO:14) and the like;

(3) for tyrosinase-derived peptides, MLLAVLYCL (SEQ ID NO:15), YMDGTMSQV (SEQ ID NO:16), AFLPWHRLF (SEQ ID NO:17), AFLPWHRLFL (SEQ ID NO:18) and the like;

(4) for CEA-derived peptides, YLSGANLNL (SEQ ID NO:19), IMIGVLVGV (SEQ ID NO:20), LLTFWNPPT (SEQ ID NO:21), QYSWFVNGTF (SEQ ID NO:22), TYACFVSNL (SEQ ID NO:23) and the like;

(5) for PSA-derived peptides, FLTPKKLQCV (SEQ ID NO:24), VSHSFPHPLY (SEQ ID NO:25), VISNDVCAQV (SEQ ID NO:26), CYASGWGSI (SEQ ID NO:27) and the like;

(6) for MUC-1-derived peptides, STAPPVHNV (SEQ ID NO:28) and the like;

(7) for HER2/neu-derived peptides, QIISAVVGIL (SEQ ID NO:29), QLFEDNYAL (SEQ ID NO:30), KIFGSLAFL (SEQ ID NO:31), CLTSVQLV (SEQ ID NO:32), VMAGVGSPYV (SEQ ID NO:33), RLLQETELV (SEQ ID NO:34), PYVSRLLGI (SEQ ID NO:35), TYLPTNASL (SEQ ID NO:36) and the like;

(8) for MAGE-1-derived peptides, NYKHCFPEI (SEQ ID NO:37) and the like;

(9) for MAGE-3-derived peptides, FLWGPRALV (SEQ ID NO:38), KVAELVHFL (SEQ ID NO:39), IMPKAGLLI (SEQ ID NO:40), TFPDLESEF (SEQ ID NO:41) and the like;

(10) for NY-ESO-1-derived peptides, SLLMWITQC (SEQ ID NO:42), SLLMWITQCFL (SEQ ID NO:43), QLSLLMWIT (SEQ ID NO:44) and the like;

(11) for SART-1-derived peptides, EYRGFTQDF (SEQ ID NO:45) and the like;

(12) for SART-3-derived peptides, VYDYNCHVDL (SEQ ID NO:46) and the like;

(13) for TERT-derived peptides, ILAKFLHWL (SEQ ID NO:47), VYAETKHFL (SEQ ID NO:48), VYGFVRACL (SEQ ID NO:49) and the like;

(14) for WT1-derived peptides, RMFPNAPYL (SEQ ID NO:50), CMTWNQMNL (SEQ ID NO:51), RWPSCQKKF (SEQ ID NO:52) and the like;

(15) for Survivin-2B-derived peptides, AYACNTSTL (SEQ ID NO:53) and the like:

In this description, the left end of each of the above-described peptides indicates the N terminus thereof, and the individual amino acid symbols show the following amino acid residues, respectively.

| | |
|---|---|
| A: | Alanine residue |
| G: | Glycine residue |
| M: | Methionine residue |
| S: | Serine residue |
| C: | Cysteine residue |
| H: | Histidine residue |
| N: | Asparagine residue |
| T: | Threonine residue |
| D: | Aspartic acid residue |
| I: | Isoleucine residue |
| P: | Proline residue |

-continued

| V: | Valine residue |
|---|---|
| E: | Glutamic acid residue |
| K: | Lysine residue |
| Q: | Glutamine residue |
| W: | Tryptophan residue |
| F: | Phenylalanine residue |
| L: | Leucine residue |
| R: | Arginine residue |
| Y: | Tyrosine residue |

These cancer antigen peptides are partial peptides of cancer antigen proteins, and some of them have cysteine at the N terminus of the amino acid sequence thereof. Such a cancer antigen peptide is likely to dimerize in water, and part or almost all of its content often has dimerized at the time of administration. In the present invention, even if a peptide having 8 to 12 amino acids dimerizes as described above, it exhibits similar CTL induction activity; therefore, a cancer antigen peptide can be chosen from among cancer antigen peptides having 8 to 12 amino acids or a dimer thereof according to the intended use. To efficiently induce CTL in vivo, the cancer antigen peptide in the present invention is preferably an epitope sequence restricted by HLA-A2402 (also simply referred to as HLA-A24) or HLA-A0201 (also simply referred to as HLA-A2) out of the cancer antigen peptides having 8 to 12 amino acids. By using such a cancer antigen peptide, an effective cancer vaccine composition that eventually induces and activates cytotoxic T cells in vivo can be prepared.

The concentration of the cancer antigen peptide (including a dimer thereof; the same applies below) in the water phase when mixed with the emulsified composition for dilution of the present invention may be chosen according to the kind of peptide used so that the content in the finally obtained cancer vaccine composition will fall in the appropriate range for activating CTL induction. The cancer vaccine composition or specific CTL inducer of the present invention (hereinafter also simply referred to as cancer vaccine composition) can be kept stable irrespective of the kind and properties of the peptide by using an emulsified composition for dilution, and the peptide concentration to be contained can be set in a broad range. Specifically, although it varies depending on the route of administration and methods of administration, usually, the peptide concentration in the finally obtained cancer vaccine composition is 0.01 to 100 mg/mL.

Regarding the route of administration of the cancer vaccine composition of the present invention, a method of administration in common use may be chosen, as long as activation of CTL induction specific for the cancer antigen peptide used is possible. As examples of the route of administration, subcutaneous, intradermal, intramuscular and the like can be mentioned.

The dose of the cancer antigen peptide can be adjusted as appropriate according to the disease to be treated, the patient's symptoms, age, body weight, sex and the like, and is 0.001 to 100 mg, more preferably 0.01 to 10 mg; this dose is preferably administered once per several days to several months.

The cancer vaccine composition of the present invention is a W/O emulsion. The cancer vaccine composition of the present invention is a W/O emulsion comprising ingredient A at 30 to 80% by weight, ingredient B at 0.5 to 20% by weight, ingredient C at 0 to 20% by weight, and ingredient E at 10 to 60% by weight, preferably comprising ingredient A at 40 to 60% by weight, ingredient B at 1.0 to 5.0% by weight, ingredient C at 5.0 to 10.0% by weight, and ingredient E at 30 to 50% by weight. Considering the preservation and administration using a syringe for injection, the cancer vaccine composition of the present invention is preferably liquid at 5° C., and preferably has a viscosity at 25° C. of not more than 300 mPa·s, more preferably not more than 200 mPa·s.

In the water phase that is the ingredient E of the present invention, a stabilizer, a solvent, a solubilizer, a suspending agent, a diluent, a buffering agent, a tonicity agent, an acidifying agent, an alkalizing agent and the like may be contained according to the properties of the cancer antigen peptide, as long as they do not influence the stability of the finally obtained cancer vaccine composition. Therefore, when a water phase comprising an antigen peptide is diluted with an emulsified composition for dilution, each of the above-described excipients may be chosen as appropriate according to the properties of the antigen peptide.

The cancer vaccine composition of the present invention stimulates CTL induction specific for the cancer antigen peptide contained, and attacks cancer cells.

CTL induction activity can be confirmed by counting the number of CTLs by the HLA tetramer method (Int. J. Cancer: 100, 565-570 (2002)) or limited dilution method (Nat. Med.: 4, 321-327 (1998)). Alternatively, for example, HLA-A24-restricted CTL induction activity can be confirmed by using the HLA-A24 model mouse described in the pamphlet for International Patent Publication No. 02/47474 and Int. J. Cancer: 100, 565-570 (2002), and the like.

The cancer vaccine composition of the present invention has the capability of inducing specific CTL according to the cancer antigen peptide contained; the CTL induced exhibits cytotoxic action and anticancer action via lymphokine production. Therefore, the cancer vaccine composition of the present invention can be used as a cancer immunotherapy preparation for the treatment or prevention of cancer.

EXAMPLES

The present invention is hereinafter described in more detail by means of the following Examples, which, however, are not to be construed as limiting the scope of the invention.
<Preparation of Emulsified Composition for Dilution>

Example 1

Ethyl oleate (a supply conforming to the Japanese Pharmaceutical Excipients) as ingredient A, polyoxyethylene (10) hardened castor oil (a supply conforming to the Japanese Pharmaceutical Excipients; 10 mol of ethylene oxide adduct) as ingredient B, and sorbitan sesquioleate (a supply conforming to the Japanese Pharmacopoeia) as ingredient C were mixed in the amounts shown in Table 1, respectively. Next, while stirring this mixture, water for injection (a supply conforming to the Japanese Pharmacopoeia) as ingredient D was gradually added in the amounts shown in Table 1. Emulsification was performed by stirring using CLEARMIX 1.5S (manufactured by M-TECHNIQUE Co., Ltd.) at 10,000 rpm for 5 minutes at room temperature. Thereby, an emulsified composition for dilution 1 was obtained. When this emulsified composition was allowed to stand at room temperature for 24 hours after preparation, no change in the appearance was observed.

Examples 2 to 35

In the same manner as Example 1, the ingredients other than ingredient D were previously mixed. While stirring this mixture, ingredient D was gradually added and emulsification was performed. In all cases, emulsification was performed by stirring using CLEARMIX 1.5S (manufactured by M-TECHNIQUE Co., Ltd.) at 10,000 rpm for 5 minutes at room temperature. As ingredient D, water for injection, 10 mM phosphate-buffered solution (pH 7.4), and 10 mM phosphate-buffered saline (pH 7.4) were used respectively according to Tables 1 to 7. Each ingredient shown in Tables 1 to 7 were supplies conforming to the Japanese Pharmacopoeia, the Japanese Pharmaceutical Excipients, or Japanese Standards of Cosmetic Ingredients. Thereby, emulsified compositions 2 to 35 were obtained. When the emulsified compositions for dilution 2 to 35 obtained were allowed to stand at room temperature for 24 hours after preparation, and examined for appearance change; no change such as separation was observed in any of the emulsified compositions.

Comparative Examples 1 to 25

In the same manner as Example 1, ethyl oleate (a supply conforming to the Japanese Pharmaceutical Excipients), the various polyoxyethylene hardened castor oils shown in Tables 8 to 12 (supplies conforming to the Japanese Pharmaceutical Excipients), and sorbitan sesquioleate (a supply conforming to the Japanese Pharmacopoeia) were mixed to obtain the amounts shown in Tables 8 to 12, respectively. Polyoxyethylene (40) hardened castor oil, polyoxyethylene (60) hardened castor oil and the like were mixed in a state molten by heating at 50° C. Because the polyoxyethylene (160) polyoxypropylene (30) glycol used to prepare an emulsified composition 46 (Comparative Example 11) is not easy to mix, it was previously dissolved in a water phase and mixed at the time of emulsification. Next, while stirring this, water for injection, 10 mM phosphate-buffered solution (pH 7.4), and 10 mM phosphate-buffered saline (pH 7.4) were gradually added according to Tables 8 to 12, respectively. Emulsification was performed by stirring using CLEARMIX 1.5S (manufactured by M-TECHNIQUE Co., Ltd.) at 10,000 rpm for 5 minutes at room temperature. Thereby, emulsified compositions for dilution 36 to 60 were obtained. Each ingredient shown in the Tables was supplies conforming to the Japanese Pharmacopoeia, the Japanese Pharmaceutical Excipients, or Japanese Standards of Cosmetic Ingredients. For the ingredients not listed in any of these compendia, supplies of pharmaceutical grade were used. When each emulsified composition obtained was allowed to stand for 24 hours after preparation, no change such as separation was observed in the emulsified compositions 36 to 39, 56 and 57, but separation of the oil phase and the water phase (including creaming) was observed in the emulsified compositions 40 to 55 and 58 to 60.

TABLE 1

| | Example | | | | |
|---|---|---|---|---|---|
| | 1 | 2 | 3 | 4 | 5 |
| | Emulsified composition number | | | | |
| | 1 | 2 | 3 | 4 | 5 |
| Ethyl oleate | 70.0 | 70.0 | — | 70.0 | 70.0 |
| Cetyl 2-ethylhexanoate | — | — | 70.0 | — | — |
| Polyoxyethylene (10) hardened castor oil | 3.0 | 3.0 | 3.0 | 3.0 | 3.0 |
| Sorbitan sesquioleate | 12.0 | — | — | 12.0 | — |
| Sorbitan monooleate | — | 12.0 | 12.0 | — | 12.0 |
| Water for injection | 15.0 | 15.0 | 15.0 | — | — |
| Phosphate-buffered saline (pH 7.4) | — | — | — | 15.0 | 15.0 |
| Change in state after being allowed to stand at room temperature for 24 hours | None | None | None | None | None |

TABLE 2

| | Example | | | | |
|---|---|---|---|---|---|
| | 6 | 7 | 8 | 9 | 10 |
| | Emulsified composition number | | | | |
| | 6 | 7 | 8 | 9 | 10 |
| Ethyl oleate | 70.0 | 70.0 | 70.0 | 70.0 | 70.0 |
| Polyoxyethylene (5) hardened castor oil | — | 3.0 | — | — | — |
| Polyoxyethylene (10) hardened castor oil | 3.0 | — | 3.0 | — | — |
| Polyoxyethylene (10) castor oil | — | — | — | 3.0 | — |
| Polyoxyethylene (20) hardened castor oil | — | — | — | — | 3.0 |
| Sorbitan sesquioleate | — | 6.0 | 6.0 | 6.0 | 6.0 |
| Glycerin monooleate | 12.0 | 6.0 | 6.0 | 6.0 | 6.0 |
| Phosphate-buffered solution (pH 7.4) | 15.0 | 15.0 | 15.0 | 15.0 | 15.0 |
| Change in state after being allowed to stand at room temperature for 24 hours | None | None | None | None | None |

TABLE 3

| | Example | | | | |
|---|---|---|---|---|---|
| | 11 | 12 | 13 | 14 | 15 |
| | Emulsified composition number | | | | |
| | 11 | 12 | 13 | 14 | 15 |
| Ethyl oleate | 70.0 | — | — | — | — |
| Cetyl 2-ethylhexanoate | — | 70.0 | — | — | — |
| Octyldodecyl myristate | — | — | 70.0 | — | — |
| 2-ethylhexyl palmitate | — | — | — | 70.0 | — |
| Oleyl oleate | — | — | — | — | 70.0 |
| Polyoxyethylene (10) hardened castor oil | 2.0 | 3.0 | 3.0 | — | — |
| Polyoxyethylene (20) hardened castor oil | 1.0 | — | — | 3.0 | 3.0 |
| Sorbitan sesquioleate | 12.0 | 6.0 | 6.0 | 6.0 | 6.0 |
| Glycerin monooleate | — | 6.0 | 6.0 | 6.0 | 6.0 |
| Water for injection | 15.0 | 15.0 | 15.0 | 15.0 | 15.0 |
| Change in state after being allowed to stand at room temperature for 24 hours | None | None | None | None | None |

TABLE 4

| | Example | | | | |
|---|---|---|---|---|---|
| | 16 | 17 | 18 | 19 | 20 |
| | Emulsified composition number | | | | |
| | 16 | 17 | 18 | 19 | 20 |
| Cetyl 2-ethylhexanoate | 70.0 | 70.0 | — | — | — |
| Ethyl oleate | — | — | 70.0 | 70.0 | — |
| Octyldodecyl myristate | — | — | — | — | 70.0 |
| Polyoxyethylene (10) hardened castor oil | 3.0 | — | 2.0 | 5.0 | 3.0 |
| Polyoxyethylene (20) hardened castor oil | — | 3.0 | 1.0 | — | — |
| Sorbitan sesquioleate | 6.0 | 12.0 | 6.0 | 6.0 | 11.0 |
| Glycerin monooleate | 5.0 | — | 5.0 | 5.0 | — |
| Glycerin | 1.0 | — | 1.0 | 1.0 | 1.0 |
| Phosphate-buffered solution (pH 7.4) | 15.0 | 15.0 | 15.0 | 15.0 | 15.0 |
| Change in state after being allowed to stand at room temperature for 24 hours | None | None | None | None | None |

TABLE 5

| | Example | | | | |
|---|---|---|---|---|---|
| | 21 | 22 | 23 | 24 | 25 |
| | Emulsified composition number | | | | |
| | 21 | 22 | 23 | 24 | 25 |
| Ethyl oleate | 70.0 | — | — | 70.0 | 70.0 |
| Cetyl 2-ethylhexanoate | — | 70.0 | — | — | — |
| Octyldodecyl myristate | — | — | 70.0 | — | — |
| Polyoxyethylene (10) hardened castor oil | 15.0 | 15.0 | 15.0 | 15.0 | 15.0 |
| Water for injection | 15.0 | 15.0 | 15.0 | — | — |
| Phosphate-buffered water (pH 7.4) | — | — | — | 15.0 | 15.0 |
| Change in state after being allowed to stand at room temperature for 24 hours | None | None | None | None | None |

TABLE 6

| | Example | | | | |
|---|---|---|---|---|---|
| | 26 | 27 | 28 | 29 | 30 |
| | Emulsified composition number | | | | |
| | 26 | 27 | 28 | 29 | 30 |
| Cetyl 2-ethylhexanoate | 75.0 | 75.0 | — | — | — |
| Ethyl oleate | — | — | 75.0 | 75.0 | 75.0 |
| Polyoxyethylene (5) hardened castor oil | — | — | 3.5 | — | — |
| Polyoxyethylene (10) hardened castor oil | 14.0 | 3.0 | — | 3.0 | — |
| Polyoxyethylene (20) hardened castor oil | — | — | — | — | 2.5 |
| Sorbitan sesquioleate | — | 6.0 | 6.5 | 12.0 | 11.5 |
| Glycerin monooleate | — | 6.0 | 5.0 | — | — |
| Glycerin | 1.0 | — | — | — | 1.0 |
| Phosphate-buffered water (pH 7.4) | 10.0 | 10.0 | 10.0 | 10.0 | 10.0 |
| Change in state after being allowed to stand at room temperature for 24 hours | None | None | None | None | None |

TABLE 7

| | Example | | | | |
|---|---|---|---|---|---|
| | 31 | 32 | 33 | 34 | 35 |
| | Emulsified composition number | | | | |
| | 31 | 32 | 33 | 34 | 35 |
| Ethyl oleate | 72.0 | 78.0 | 80.0 | 74.0 | — |
| Jojoba oil | — | — | — | — | 70.0 |
| Polyoxyethylene (10) hardened castor oil | 3.0 | 3.5 | 3.0 | 3.0 | 3.0 |
| Sorbitan sesquioleate | 15.0 | 7.5 | 5.0 | 15.0 | 12.0 |
| Glycerin | 1.0 | 1.0 | — | 1.0 | — |
| Phosphate-buffered water (pH 7.4) | 10.0 | 10.0 | 12.0 | 7.0 | 15.0 |
| Change in state after being allowed to stand at room temperature for 24 hours | None | None | None | None | None |

TABLE 8

| | Comparative Example | | | | |
|---|---|---|---|---|---|
| | 1 | 2 | 3 | 4 | 5 |
| | Emulsified composition number | | | | |
| | 36 | 37 | 38 | 39 | 40 |
| Ethyl oleate | 70.0 | 70.0 | — | 70.0 | 70.0 |
| Cetyl 2-ethylhexanoate | — | — | 70.0 | — | — |
| Polyoxyethylene (30) hardened castor oil | — | 3.0 | — | — | — |
| Polyoxyethylene (40) hardened castor oil | 3.0 | — | 3.0 | — | — |
| Polyoxyethylene (60) hardened castor oil | — | — | — | 3.0 | — |
| Sorbitan sesquioleate | 12.0 | 6.0 | 6.0 | 6.0 | 7.5 |
| Glycerin monooleate | — | 6.0 | 6.0 | 6.0 | 7.5 |
| Water for injection | 15.0 | 15.0 | 15.0 | 15.0 | 15.0 |
| Change in state after being allowed to stand at room temperature for 24 hours | None | None | None | None | Separated |

TABLE 9

| | Comparative Example | | | | |
|---|---|---|---|---|---|
| | 6 | 7 | 8 | 9 | 10 |
| | Emulsified composition number | | | | |
| | 41 | 42 | 43 | 44 | 45 |
| Cetyl 2-ethylhexanoate | 70.0 | — | — | — | — |
| Diethyl sebacate | — | 70.0 | — | — | — |
| Purified soybean oil | — | — | 70.0 | — | — |
| Squalane | — | — | — | 70.0 | — |
| Light liquid paraffin | — | — | — | — | 70.0 |
| Polyoxyethylene (10) hardened castor oil | — | 3.0 | 3.0 | 3.0 | 3.0 |
| Sorbitan sesquioleate | 7.5 | 6.0 | 6.0 | 6.0 | 6.0 |
| Glycerin monooleate | 7.5 | 6.0 | 6.0 | 6.0 | 6.0 |
| Water for injection | 15.0 | 15.0 | 15.0 | 15.0 | 15.0 |
| Change in state after being allowed to stand at room temperature for 24 hours | Separated | Separated | Separated | Separated | Slightly separated |

TABLE 10

| | Comparative Example | | | | |
|---|---|---|---|---|---|
| | 11 | 12 | 13 | 14 | 15 |
| | Emulsified composition number | | | | |
| | 46 | 47 | 48 | 49 | 50 |
| Ethyl oleate | 70.0 | 70.0 | 70.0 | 70.0 | 70.0 |
| Polyoxyethylene (160) polyoxypropylene (30) glycol | 3.0 | — | — | — | — |
| Polyoxyethylene (20) polyoxypropylene (20) glycol | — | 3.0 | — | — | — |
| Polyoxyethylene (6) sorbitan monooleate | — | — | 3.0 | — | — |
| Polyoxyethylene (6) sorbitol tetraoleate | — | — | — | 3.0 | — |
| Polyoxyethylene (30) sorbitol tetraoleate | — | — | — | — | 3.0 |
| Sorbitan sesquioleate | 6.0 | 6.0 | 6.0 | 6.0 | 6.0 |
| Glycerin monooleate | 6.0 | 6.0 | 6.0 | 6.0 | 6.0 |
| Phosphate-buffered water (pH 7.4) | 15.0 | 15.0 | 15.0 | 15.0 | 15.0 |
| Change in state after being allowed to stand at room temperature for 24 hours | Separated | Separated | Separated | Separated | Separated |

TABLE 11

| | Comparative Example | | | | |
|---|---|---|---|---|---|
| | 16 | 17 | 18 | 19 | 20 |
| | Emulsified composition number | | | | |
| | 51 | 52 | 53 | 54 | 55 |
| Ethyl oleate | 70.0 | 70.0 | 70.0 | — | 70.0 |
| Cetyl 2-ethylhexanoate | — | — | — | 70.0 | — |
| Polyoxyethylene (60) hardened castor oil | — | — | 15.0 | 15.0 | — |
| Polysorbate 80 | 3.0 | — | — | — | 15.0 |
| Castor oil | — | 3.0 | — | — | — |
| Sorbitan sesquioleate | 6.0 | 6.0 | — | — | — |
| Glycerin monooleate | 6.0 | 6.0 | — | — | — |
| Water for injection | 15.0 | 15.0 | 15.0 | 15.0 | 15.0 |
| Change in state after being allowed to stand at room temperature for 24 hours | Separated | Separated | Separated | Separated | Separated |

TABLE 12

| | Comparative Example | | | | |
|---|---|---|---|---|---|
| | 21 | 22 | 23 | 24 | 25 |
| | Emulsified composition number | | | | |
| | 56 | 57 | 58 | 59 | 60 |
| Cetyl 2-ethylhexanoate | 75.0 | — | — | — | — |
| Ethyl oleate | — | 75.0 | — | — | — |
| Squalane | — | — | 75.0 | — | — |
| Purified soybean oil | — | — | — | 75.0 | — |
| Tri(caprylate/caprate) glycerin | — | — | — | — | 75.0 |
| Polyoxyethylene (10) hardened castor oil | — | — | 3.0 | 3.0 | 3.0 |
| Polyoxyethylene (40) hardened castor oil | 3.0 | — | — | — | — |
| Polyoxyethylene (60) hardened castor oil | — | 3.0 | — | — | — |
| Sorbitan sesquioleate | 11.0 | — | 4.0 | 11.0 | 11.0 |
| Glycerin monooleate | — | 11.0 | 4.0 | — | — |
| Glycerin | 1.0 | 1.0 | — | 1.0 | 1.0 |
| Phosphate-buffered water (pH 7.4) | 10.0 | 10.0 | 10.0 | 10.0 | 10.0 |
| Change in state after being allowed to stand at room temperature for 24 hours | None | None | Separated | Separated | Separated |

Test Example 1

<Preparation of Cancer Vaccine Compositions>

Of the emulsified compositions for dilution obtained in the Examples, those showing no apparent separation when allowed to stand for 24 hours after preparation were used to prepare cancer vaccine compositions comprising various cancer antigen peptides. The cancer antigen peptides used for the preparation are shown in Table 13. All these peptides are HLA-A24-restricted.

TABLE 13

| Name of antigen peptide | Source protein | Amino acid positions | Amino acid sequence |
|---|---|---|---|
| TERT | Telomerase | 324-332 | VYAETKHFL (SEQ ID NO:48) |
| MAGE-1 | Melanoma antigen | 135-143 | NYKHCFPEI (SEQ ID NO:37) |
| CEA | Carcinoembryonic antigen | 652-660 | TYACFVSNL (SEQ ID NO:23) |
| PSA | Prostate-specific antigen | 152-160 | CYASGWGSI (SEQ ID NO:27) |

For TERT, MAGE-1, and CEA out of the cancer antigen peptides shown in Table 13, 1.2 mg of synthetic peptide was dissolved in 10.8 μL of DMSO, after which the solution was diluted with 349.2 μL of water for injection, and the absence of precipitate was visually confirmed (DMSO concentration 3%). For PSA, 1.2 mg of synthetic peptide was diluted with water for injection to make 360 μL, and the absence of precipitate was visually confirmed. Separately, the emulsified composition obtained in each Example was thoroughly mixed using a shikenkan mixer (Touch Mixer MT-51, manufactured by Yamato Scientific Co., Ltd.) (fully stirred and homogenized before use).

Next, 700 μL of the emulsified composition was collected in cryogenic vial inner cap type of 5 mL capacity (manufactured by Sumitomo Bakelite Co., Ltd.) using a 1000 μL Eppendorf pipette. Next, while stirring the tube using a shikenkan mixer, 300 μL of the above-described peptide-containing water phase was added drop by drop, and mixed. The stirring speed of the shikenkan mixer was set at the maximum level. After the peptide-containing water phase was added drop by drop, the mixture was further stirred using the shikenkan mixer for 2 minutes to yield a cancer vaccine composition.

In the experiments below, CTL induction activity was actually evaluated using prepared cancer vaccine compositions; unless otherwise stated, the cancer vaccine compositions used for the evaluation were prepared according to the above-described method.

Test Example 2

<CTL Induction with Cancer Vaccine Composition Comprising Tert Peptide>

The specific CTL induction potential of the cancer vaccine composition comprising the TERT peptide, prepared in Test Example 1, was evaluated using HLA-A24 transgenic mice (Int. J. Cancer: 100, 565, 2002).

To prepare cancer vaccine compositions, emulsified compositions 7, 8, 37, 38, 39, and 45 were used. The cancer vaccine compositions prepared were given the same numbers as the emulsified compositions. In the evaluation, separately from Test Example 1, groups receiving an emulsion comprising the TERT peptide, prepared using incomplete Freund's adjuvant (IFA, purchased from Wako Pure Chemical Industries, Ltd.), or the peptide water phase alone, as the dosing liquid, were established, and compared with groups receiving each cancer vaccine composition as the dosing liquid (matched to ensure that all dosing groups would receive the same dose of peptide). 200 µL of each dosing liquid (dose of each peptide 200 µg) was subcutaneously administered to the tail root of each HLA-A24/$k^b$ transgenic mouse. Three mice were used for each group. Seven to eight days after administration, the spleen was extirpated and splenocytes were prepared. Some of the splenocytes were pulsed with 100 µg/mL peptide for 1 hour. "Pulse" refers to adding a peptide to splenocytes to bind the antigen peptide to HLA on the cell surface. The splenocytes not pulsed with the peptide were sown to a 24-well plate at $7\times10^6$ cells/well, and the above splenocytes pulsed with the peptide were further added at $7\times10^5$ cells/well and cultured. The culture broth comprised an RPMI1640 medium supplemented with 10% FCS, 10 mM HEPES, 20 mM L-glutamine, 1 mM sodium pyruvate, 1 mM MEM non-essential amino acids, 1% MEM vitamin, and 55 µM 2-mercaptoethanol, and the cells were cultured for 5 to 6 days. The CTL activity specific for the peptide administered in the cultured splenocytes was measured by $^{51}$Cr release assay (J. Immunol.: 159, 4753, 1997). The target cells used were cells of the cell line EL4-A2402/$K^b$ prepared by transferring a gene to mouse lymphoma-derived cell line EL-4 cells (ATCC line number TIB-39) so that the HLA-A24 and H-2 $K^b$ chimeric MHC class I molecule (Int. J. Cancer: 100, 565, 2002) would be stably expressed. The target cells were labeled with $^{51}$Cr at 3.7 Mbq/$10^6$ cells, after which the aforementioned peptide was added to obtain a concentration of 100 µg/mL, and the cells were further pulsed for 1 hour. The target cells, but not pulsed with the peptide (non-pulsed), were labeled with $^{51}$Cr for 2 hours and used as control target cells. These labeled target cells and previously prepared splenocytes were mixed in a ratio of 1:80 and cultured for 4 hours, and CTL activity was calculated from the ratio of target cells injured. The results are shown in FIG. 1.

As shown in FIG. 1, in the groups receiving the cancer vaccine composition of the present invention, the target cells pulsed with the peptide were severely injured, but the control target cells not pulsed with the peptide were less injured; therefore, it was demonstrated that peptide specific CTL was induced. On the other hand, in the groups receiving the cancer vaccines 37, 38, 39, and 45, the group receiving the peptide emulsion prepared with IFA, and the group receiving the peptide alone, the cytotoxicity was low, and the CTL induction activity was low. From this finding, it is evident that the emulsified composition for dilution of the present invention activates in vivo CTL induction when combined with cancer antigen peptides. It is also shown that the choice of the ingredient A of the present invention and the molar number of ethylene oxide adduct to the ingredient B influence CTL induction activity.

Test Example 3

<CTL Induction with Cancer Vaccine Composition Comprising MAGE-1 Peptide>

The specific CTL induction potential of the cancer vaccine composition comprising the MAGE-1 peptide, prepared in Test Example 1, was evaluated in the same manner as Test Example 2.

To prepare cancer vaccine compositions, the emulsified compositions 8, 37, 38, and 45 were used. The cancer vaccine compositions prepared were given the same numbers as the emulsified compositions. In the evaluation, separately from Test Example 1, groups receiving an emulsion comprising the MAGE-1 peptide, prepared using incomplete Freund's adjuvant (IFA, purchased from Wako Pure Chemical Industries, Ltd.), or the peptide water phase alone, as the dosing liquid, were established, and compared with groups receiving each cancer vaccine composition as the dosing liquid. The results are shown in FIG. 2.

Figure 2:
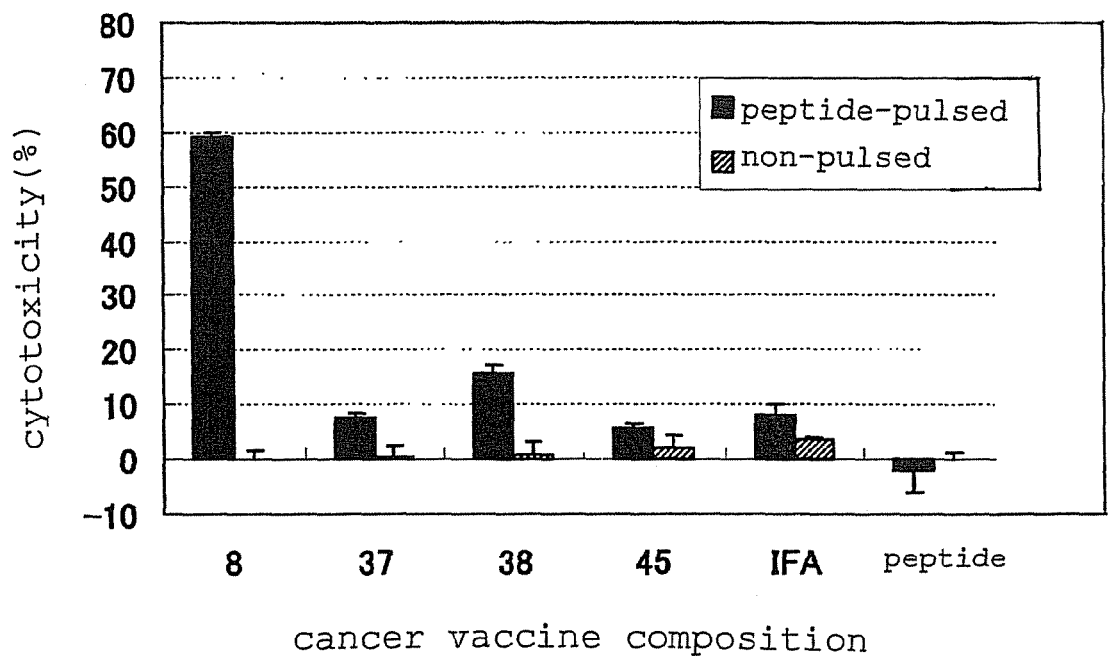
FIG. 2 is a graph showing the results of specific CTL induction using cancer vaccine compositions comprising the MAGE-1 peptide.

As shown in FIG. 2, in the group receiving the cancer vaccine composition of the present invention, the target cells pulsed with the peptide were severely injured, but the control target cells not pulsed with the peptide were less injured; therefore, it was demonstrated that peptide specific CTL was induced. On the other hand, in the groups receiving the cancer vaccines 37, 38, and 45, the group receiving the peptide emulsions prepared with IFA, and the group receiving the peptide alone, the cytotoxicity was low, and the CTL induction activity was low. These results are similar to those of Test Example 2, demonstrating the utility of the emulsified composition for dilution of the present invention.

Test Example 4

<CTL Induction with Cancer Vaccine Composition Comprising the PSA Peptide (1)>

The specific CTL induction potential of the cancer vaccine composition comprising the PSA peptide, prepared in Test Example 1, was evaluated in the same manner as Test Example 2.

To prepare cancer vaccine compositions, the emulsified compositions 2, 7, 10, 29, and 38 were used. The cancer vaccine compositions prepared were given the same numbers as the emulsified compositions. Also, using the emulsified composition 7, 700 µL of the emulsified composition and 300 µL of water for injection were mixed according to Test Example 1 to prepare a peptide-free composition, and a comparison was performed. The results are shown in FIG. 3.

Figure 3:
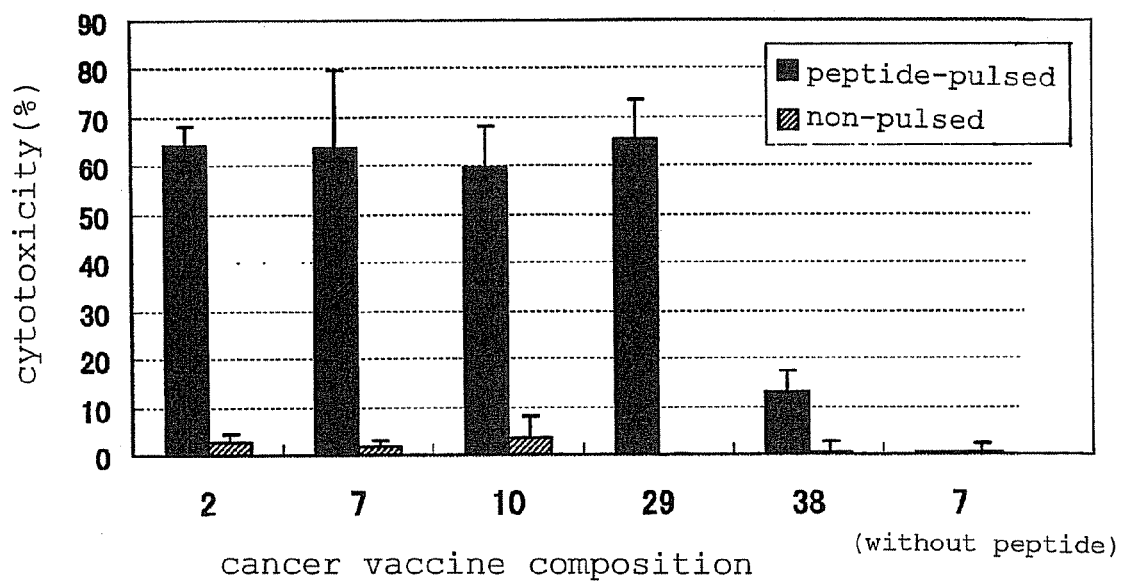
FIG. 3 is a graph showing the results of specific CTL induction using cancer vaccine compositions comprising the PSA peptide.

As shown in FIG. 3, in the groups receiving the cancer vaccine composition of the present invention (2, 7, 10, 29), the target cells pulsed with the peptide were severely injured, but the control target cells not pulsed with the peptide were less injured; therefore, it was demonstrated that peptide specific CTL was induced. On the other hand, in the group receiving the cancer vaccine 38, the cytotoxicity was low, and the CTL induction activity was low. In the group receiving the peptide-free composition, absolutely no cytotoxicity was observed, demonstrating that the emulsified composition alone does not have the activity to induce CTL. These results are similar to those of Test Example 2, demonstrating the utility of the emulsified composition for dilution of the present invention.

Test Example 5

<CTL Induction with Cancer Vaccine Composition Comprising PSA Peptide (2)>

The specific CTL induction potential of the cancer vaccine composition comprising the PSA peptide, prepared in Test Example 1, was evaluated in the same manner as Test Example 4.

To prepare cancer vaccine compositions, the emulsified compositions 16, 17, and 20 were used. The cancer vaccine compositions prepared were given the same numbers as the emulsified compositions. In the evaluation, separately from Test Example 1, a group receiving an emulsion comprising the PSA peptide, prepared using incomplete Freund's adjuvant (IFA, purchased from Wako Pure Chemical Industries, Ltd.) as the dosing liquid, was established, and compared with groups receiving each cancer vaccine composition as the dosing liquid. The results are shown in FIG. 4.

Figure 4:
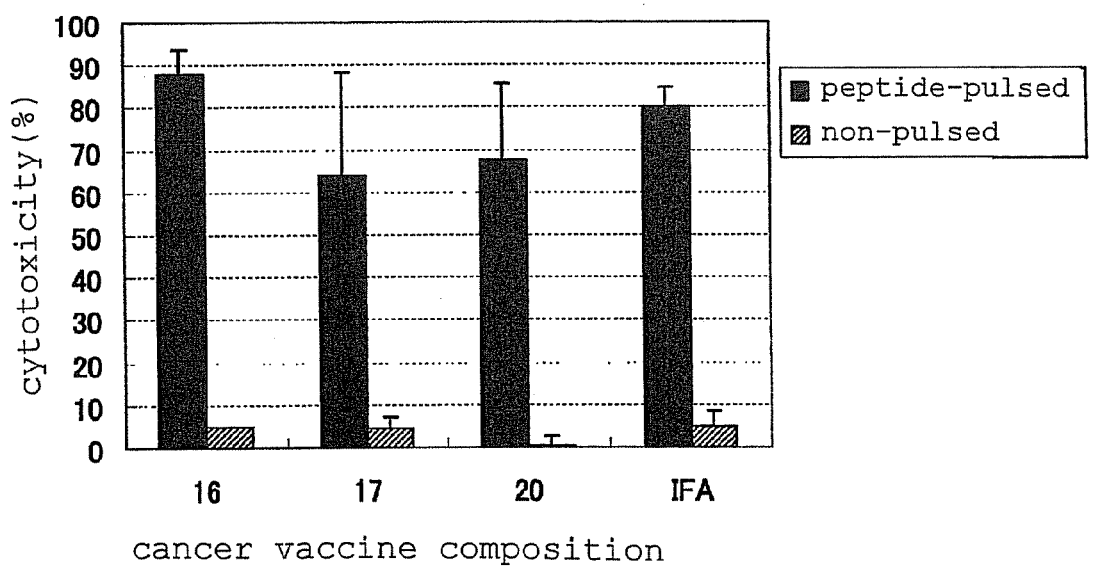
FIG. 4 is a graph showing the results of specific CTL induction using cancer vaccine compositions comprising the PSA peptide.

As shown in FIG. 4, in the group receiving the cancer vaccine composition of the present invention, the target cells pulsed with the peptide were severely injured, but the control target cells not pulsed with the peptide were less injured; therefore, it was demonstrated that peptide specific CTL was induced. When the PSA peptide was used, even in the group receiving the peptide emulsion prepared with IFA, peptide specific CTL was induced. From this result and the results of Test Examples 2 and 3, it was shown that IFA, which is conventionally known, activated CTL induction in some cancer antigen peptides, but that this activation was significantly influenced by the kind of peptide, and that IFA is insufficient in versatility.

Test Example 6

<CTL Induction with Cancer Vaccine Composition Comprising CEA Peptide>

The specific CTL induction potential of the CEA-containing cancer vaccine composition prepared in the Test Example 1 was evaluated in the same manner as Test Example 2.

Figure 5:
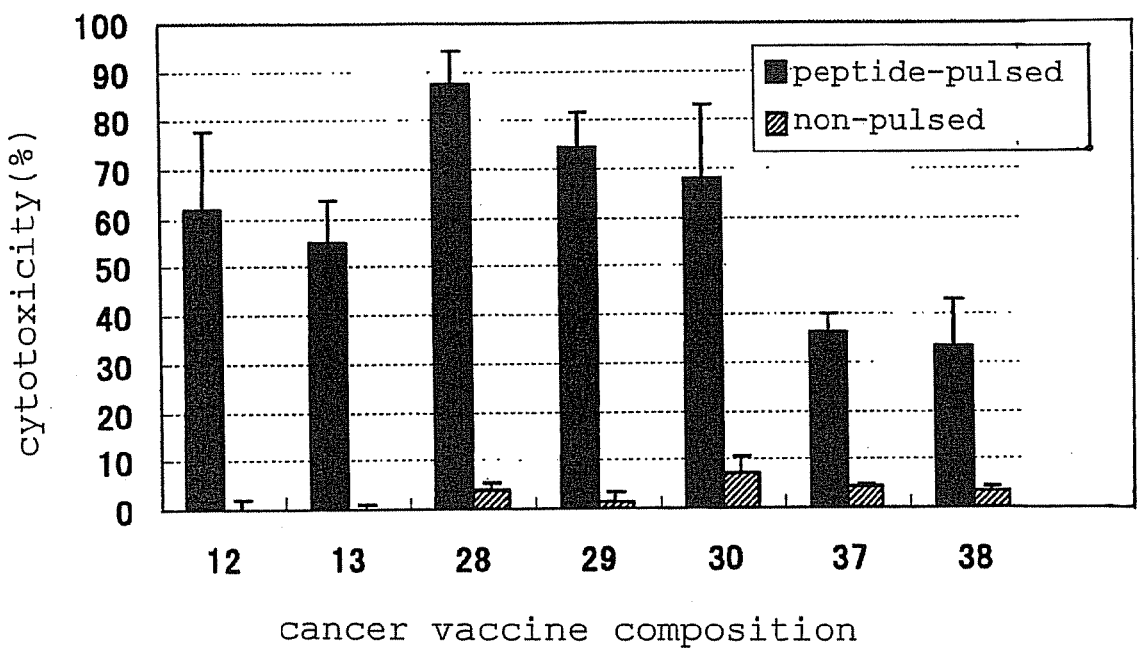
FIG. 5 is a graph showing the results of specific CTL induction using cancer vaccine compositions comprising the CEA peptide.

To prepare cancer vaccine compositions, the emulsified compositions 12, 13, 28, 29, 30, 37, and 38 were used. The cancer vaccine compositions prepared were given the same numbers as the emulsified compositions. The results are shown in FIG. 5. As shown in FIG. 5, in the groups receiving a cancer vaccine composition prepared using the emulsified composition of the present invention (12, 13, 28, 29), the target cells pulsed with the peptide were severely injured, but the control target cells not pulsed with the peptide were less injured; therefore, it was demonstrated that peptide specific CTL was induced. On the other hand, in the groups receiving the cancer vaccines 37 and 38, the cytotoxicity was low, and the CTL induction activity was low. These results are similar to those of Test Example 2, demonstrating the utility of the emulsified composition for dilution of the present invention.

Test Example 7

<CTL Induction with Cancer Vaccine Compositions Comprising Various Cancer Antigen Peptides>

Figure 6:
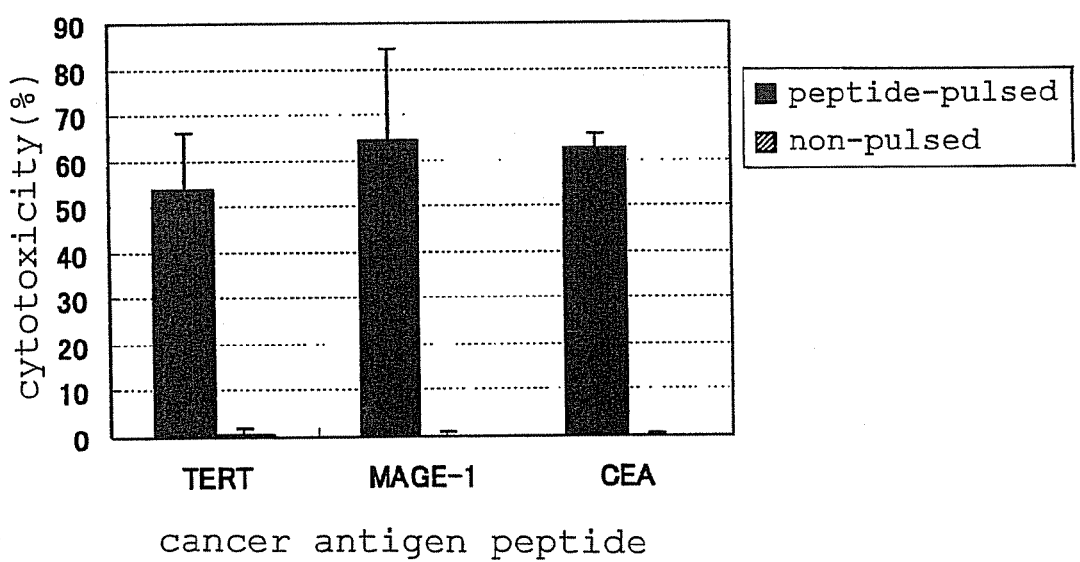
FIG. 6 is a graph showing the results of specific CTL induction using cancer vaccine compositions comprising various cancer antigen peptides.

Using the emulsified composition 21, the specific CTL induction potentials of the cancer vaccine compositions comprising each of the TERT, MAGE-1, and CEA peptides, prepared according to Test Example 1, were evaluated in the same manner as Test Example 2. The results are shown in FIG. 6. According to FIG. 6, in the group receiving a cancer vaccine composition prepared using the emulsified composition of the present invention, the target cells pulsed with the peptide were severely injured, but the control target cells not pulsed with the peptide were less injured; therefore, it was demonstrated that peptide specific CTL was induced.

These results show that the emulsified composition for dilution of the present invention activates CTL induction specific for each cancer antigen in vivo when combined with various cancer antigen peptides.

Test Example 8

<Evaluation of Stability of Emulsified Compositions for Dilution>

Emulsified compositions for dilution prepared in Examples were tested for stability. For the test, the emulsified compositions 1 to 39, 56, and 57, which showed no apparent separation when allowed to stand for 24 hours after preparation, were used. Specifically, 2 mL of each emulsified composition was filled in a glass vial of 4 mL capacity, and the vial was tightly closed and stored at 25° C. for 1 month, 3 months, and 6 months, after which each composition was examined for apparent change. As a result, no apparent change was observed in any of the emulsified compositions.

Test Example 9

<Microscopic Examination of Emulsified Compositions for Dilution>

In the same manner as Test Example 8, the emulsified compositions showing no apparent separation when allowed to stand for 24 hours after preparation (1 to 39, 56, 57) were used to microscopically examine the emulsified state both before and after dilution. First, the emulsified state of each emulsified composition was examined using a phase contrast microscope at 200-fold magnification. As a result, all emulsified compositions exhibited a fine good emulsified state. Hence, 700 μL of each emulsified composition and 300 μL of water for injection were taken in cryogenic vial inner cap type of 5 mL capacity (manufactured by Sumitomo Bakelite Co., Ltd.), and stirred using a shikenkan mixer (Touch Mixer MT-51, manufactured by Yamato Scientific Co., Ltd.) for 2 minutes, after which each composition was examined for emulsified state under microscope in the same manner as above. As a result, the emulsified compositions 1 to 35 exhibited a fine good emulsified state, whereas the emulsified compositions 36 to 39, 56 and 57 exhibited evident aggregation of water phase particles.

Test Example 10

<Evaluation of Average Particle Diameters of Emulsified Compositions for Dilution>

Figure 7:
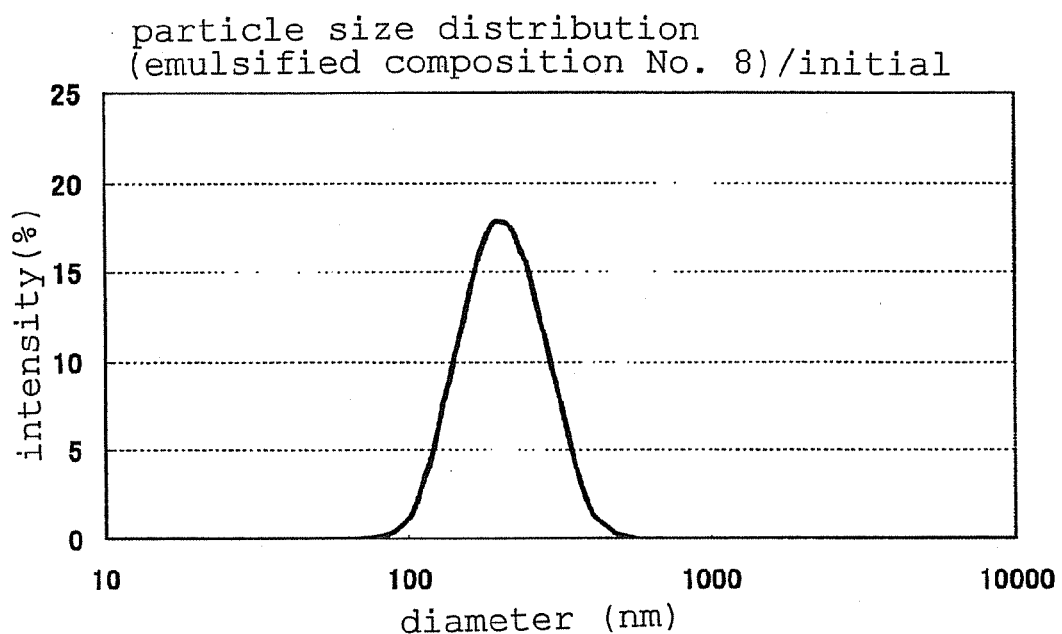
FIG. 7 shows the particle size distribution of emulsified composition for dilution 8.
Figure 8:
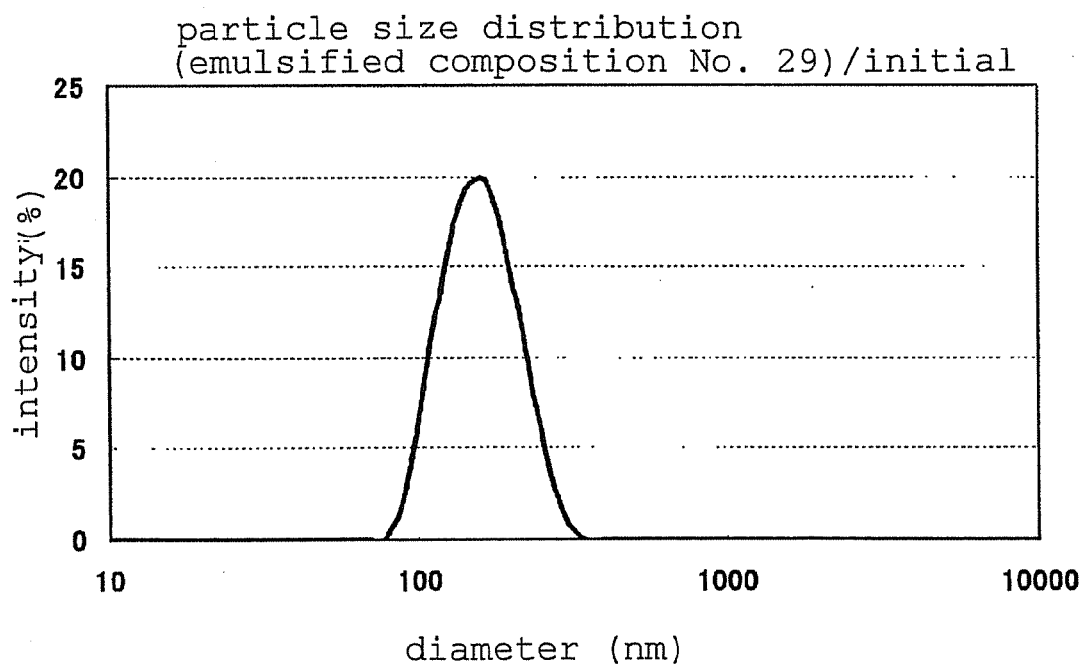
FIG. 8 shows the particle size distribution of emulsified composition for dilution 29.

Of the emulsified compositions for dilution obtained in the Examples and Comparative Examples, the emulsified compositions 1, 2, 4, 6, 7, 8, 10, 21, 29, 36, and 39 were tested to determine the average particle diameters thereof. Measurements were performed by the dynamic light scattering method using a particle size distribution analyzer (ZETASIZER NANO-S, manufactured by MALVERN INSTRUMENTS Company). To ensure accurate measurements, each emulsified composition was diluted as appropriate with a continual phase of ethyl oleate at the time of measurement. The results are shown in Table 14. Each average particle diameter is the mean of all particle diameters calculated from the light scattering intensity. As examples of the measurement results, the particle size distributions of the emulsified compositions 8 and 29 at the time of preparation (initial) are shown in FIGS. 7 and 8, respectively.

TABLE 14

| Emulsified composition | Average particle diameter (nm) | |
|---|---|---|
| | At time of preparation (initial) | After storage at 5° C. for 3 months |
| 1 | 181 | 179 |
| 2 | 195 | 203 |
| 4 | 233 | 252 |
| 6 | 266 | 275 |
| 7 | 388 | 420 |
| 8 | 192 | 189 |
| 10 | 163 | 171 |
| 21 | 78 | 81 |
| 29 | 150 | 132 |
| 36 | 208 | |
| 39 | 160 | |

As a result of the measurements, all emulsified compositions had an average particle diameter in the range of 50 to 500 nm at the time of preparation. From this finding, it is seen that simply exhibiting a good emulsified state is insufficient to use for diluting cancer antigen peptides. Hence, this data showed that what is essential to the CTL induction potential of the emulsified composition for dilution of the present invention is not "to be capable of preparing a good emulsified composition", but for the molar number of ethylene oxide adduct to the ingredient B nonionic surfactant to fall in a particular range.

For the emulsified compositions 1, 2, 4, 6, 7, 8, 10, 21, and 29 out of the above-described emulsified compositions for dilution, average particle diameters after storage at 5° C. for 3 months were measured in the same manner. As a result, no major change in average particle diameter was observed in any of the emulsified compositions; therefore, it is seen that the emulsified composition for dilution of the present invention is also excellent in low-temperature stability.

Test Example 11

<CTL Induction with Cancer Vaccine Compositions Comprising a Mixture of Two Kinds of Cancer Antigen Peptide>

Cancer vaccine compositions comprising each of mixtures of two kinds of peptides, i.e., MAGE-1 and CEA, TERT and CEA, and CEA and PSA, out of the cancer antigen peptides described in Table 13, were prepared, and the specific CTL induction potentials thereof were evaluated.

Each cancer vaccine composition was prepared using the emulsified composition 4, specifically as described below.

First, each of the MAGE-1, CEA, TERT, and PSA peptides was prepared as a 100 mg/mL DMSO solution. Next, each of the combinations of MAGE-1 and CEA, TERT and CEA, CEA and PSA in DMSO solution was mixed, and each mixture was diluted using water for injection to obtain a concentration of 2 mg/600 μL for each peptide to yield peptide mixed solutions (4 mg/600 μL as the total amount of peptide). After preparation of each solution, the absence of precipitate was visually confirmed. Separately, emulsified compositions obtained in Examples were thoroughly mixed using a shikenkan mixer (Touch Mixer MT-51, manufactured by Yamato Scientific Co., Ltd.) (fully stirred and homogenized before use).

Next, 700 μL of the emulsified composition was collected in cryogenic vial inner cap type of 5 mL capacity (manufactured by Sumitomo Bakelite Co., Ltd.) using a 1000 μL Eppendorf pipette. Next, while stirring the tube using the shikenkan mixer, 300 μL of the above-described peptide mixed solution was added drop by drop, and mixed. The stirring speed of the shikenkan mixer was set at the maximum level. After the peptide mixed solution was added drop by drop, the mixture was further stirred for 2 minutes using the shikenkan mixer to yield three kinds of cancer vaccine compositions (MAGE-1/CEA mixture, TERT/CEA mixture, CEA/PSA mixture).

The specific CTL induction potentials of the three kinds of cancer vaccine composition prepared were evaluated using HLA-A24 transgenic mice (Int. J. Cancer: 100, 565, 2002).

200 μL of each dosing liquid (each peptide dose of 200 μg×2 kinds) was subcutaneously administered to the tail root of each HLA-A24/$K^b$ transgenic mouse. One mouse was used for each group. Seven days after administration, the spleen was extirpated and splenocytes were prepared. Some of the splenocytes were pulsed with 50 μg/mL of each of two kinds of subject peptides (100 μg/mL in total) for 1 hour. Splenocytes not pulsed with the peptides were sown to a 24-well plate at 7×10$^6$ cells/well, and the above-mentioned splenocytes pulsed with the peptide were further added at 7×10$^5$ cells/well and cultured. The culture broth comprised an RPMI1640 medium supplemented with 10% FCS, 10 mM HEPES, 20 mM L-glutamine, 1 mM sodium pyruvate, 1 mM MEM non-essential amino acids, 1% MEM vitamin, and 55 μM 2-mercaptoethanol, and the cells were cultured for 5 days. The CTL activity specific for the peptide administered in the cultured splenocytes was measured by $^{51}$Cr release assay (J. Immunol.: 159, 4753, 1997). The target cells used were cells of the cell line EL4-A2402/$K^b$ prepared by transferring a gene to mouse lymphoma-derived cell line EL-4 cells (ATCC line number TIB-39) so that the HLA-A24 and H-2 $K^b$ chimeric MHC class I molecule (Int. J. Cancer: 100, 565, 2002) would be stably expressed. The target cells were labeled with $^{51}$Cr at 3.7 Mbq/10$^6$ cells, after which each peptide was added to obtain a concentration of 100 μg/mL, and the cells were pulsed for 1 hour. Target cells not pulsed with the peptide (non-pulsed) were labeled with $^{51}$Cr for 2 hours and served as control target cells. These labeled target cells and previously prepared splenocytes were mixed in a ratio of 1:80 and cultured for 4 hours, and CTL activity was determined from the ratio of target cells injured. The results are shown in FIG. 9.

Figure 9:
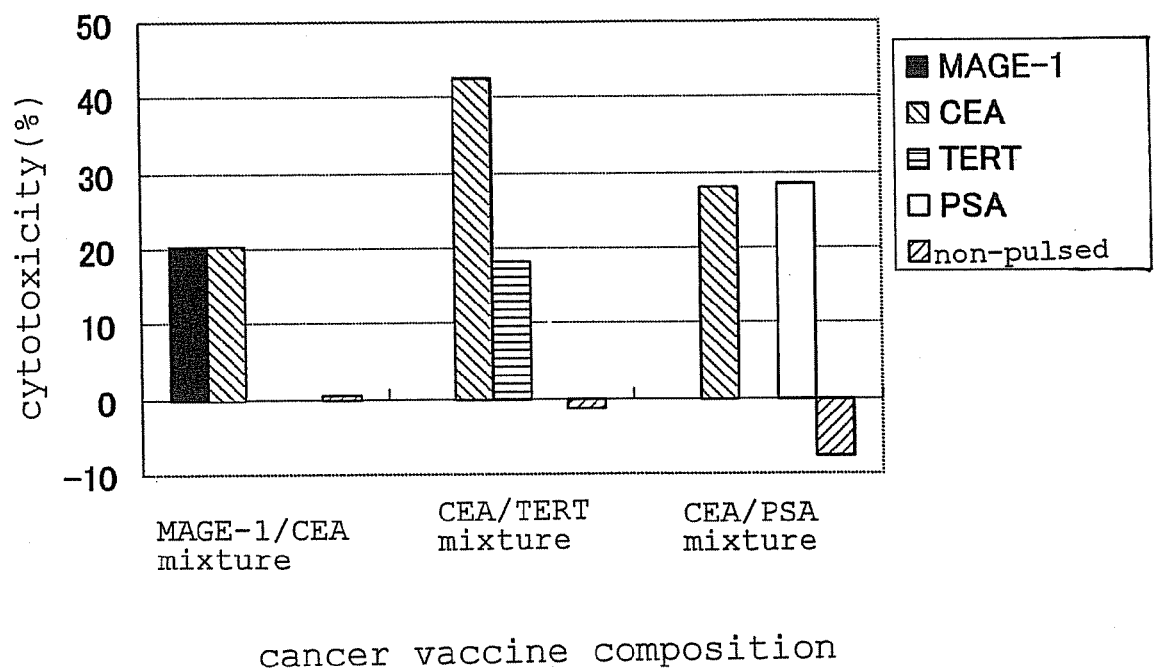
FIG. 9 is a graph showing the results of specific CTL induction to each peptide using cancer vaccine compositions comprising a mixture of two kinds of cancer antigen peptide.

As shown in FIG. 9, in the groups receiving cancer vaccine compositions prepared using the emulsified composition for dilution of the present invention, the target cells pulsed with the peptides were severely injured. On the other hand, the control target cells not pulsed with the peptides were less injured; therefore, it was demonstrated that when two kinds of cancer antigen peptide were mixed, CTL specific for each peptide was concurrently induced. From this finding, it was demonstrated that the emulsified composition for dilution of the present invention activates CTL induction in vivo when combined with various cancer antigen peptides.

Industrial Applicability

The emulsified composition for dilution of the present invention is a stable W/O emulsion per se. By diluting a cancer antigen peptide or a dimer thereof with the emulsified composition for dilution of the present invention by a simple operation, there is provided a cancer vaccine composition that is a stable W/O emulsion exhibiting CTL induction activity specific for each cancer antigen in vivo.

The present invention also provides an emulsified composition for diluting a cancer antigen peptide or a dimer thereof, intended to induce specific CTL. Also provided by this emulsified composition for dilution is a cancer vaccine composition having CTL induction activity specific for various cancer antigens in vivo. The present invention is considered to be effective in ameliorating conditions in many cancer patients.

This application is based on a patent application No. 2005-012140 filed in Japan on Jan. 19, 2005, the contents of which are incorporated in full herein by this reference.

The invention claimed is:

1. An emulsified composition for diluting a cancer antigen peptide having 8 to 12 amino acids or a dimer thereof, comprising:
   (A) 50 to 90% by weight ester of a fatty acid having 8 to 22 carbon atoms and an alcohol having 2 to 24 carbon atoms, the ester having a solidification point of not more than 10° C.,
   (B) 0.5 to 20% by weight nonionic surfactant consisting of a hydroxy fatty acid triglyceride adduct with 5 to 20 mol of ethylene oxide,
   (C) 1 to 20% by weight emulsifier that is a partial ester of a polyhydric alcohol and a fatty acid, the partial ester being liquid at 40° C., and
   (D) 5 to 20% by weight water.

2. An emulsified composition for diluting a cancer antigen peptide having 8 to 12 amino acids or a dimer thereof, comprising:
   (A) 50 to 90% by weight ester of a fatty acid having 8 to 22 carbon atoms and an alcohol having 2 to 24 carbon atoms, the ester having a solidification point of not more than 10° C.,
   (B) 0.5 to 20% by weight nonionic surfactant consisting of a hydroxy fatty acid triglyceride adduct with 5 to 20 mol of ethylene oxide,
   (C) 0 to 20% by weight emulsifier that is a partial ester of a polyhydric alcohol and a fatty acid, the partial ester being liquid at 40° C., and
   (D) 5 to 20% by weight water,
   wherein the average particle diameter of the dispersion phase of the emulsified composition for dilution is 50 to 500 nm.

3. The emulsified composition for dilution of claim 2, wherein the fatty acid of (A) is oleic acid, myristic acid or 2-ethylhexanoic acid.

4. The emulsified composition for dilution of claim 2, wherein the ester of (A) is ethyl oleate, octyldodecyl myristate or cetyl 2-ethylhexanoate.

5. The emulsified composition for dilution of claim 2, wherein the hydroxy fatty acid triglyceride of (B) is castor oil or hardened castor oil.

6. A method of preparing a cancer vaccine composition, comprising diluting 0.25 to 1 part by volume of a water phase comprising a cancer antigen peptide having 8 to 12 amino acids or a dimer thereof with 1 part by volume of an emulsified composition for dilution comprising (A) 50 to 90% by weight ester of a fatty acid having 8 to 22 carbon atoms and an alcohol having 2 to 24 carbon atoms, the ester having a solidification point of not more than 10° C., (B) 0.5 to 20% by weight nonionic surfactant consisting of a hydroxy fatty acid triglyceride adduct with 5 to 20 mol of ethylene oxide, (C) 0 to 20% by weight emulsifier that is a partial ester of a polyhydric alcohol and a fatty acid, the partial ester being liquid at 40° C., and (D) 5 to 20% by weight water.

7. A method of preparing a cancer vaccine composition, comprising diluting 0.25 to 1 part by volume of a water phase comprising a cancer antigen peptide having 8 to 12 amino acids or a dimer thereof with 1 part by volume of the emulsified composition for dilution of claim 2.

8. The emulsified composition for dilution of claim 2, wherein the nonionic surfactant of (B) consists of a hydroxy fatty acid triglyceride adduct with 10 to 20 mol of ethylene oxide.

9. The emulsified composition for dilution of claim 2, comprising the emulsifier of (C) at 1 to 20% by weight.

10. A cancer vaccine composition comprising:
   (A) 30 to 80% by weight ester of a fatty acid having 8 to 22 carbon atoms and an alcohol having 2 to 24 carbon atoms, the solidification point of the ester being not more than 10° C.,
   (B) 0.5 to 20% by weight nonionic surfactant consisting of a hydroxy fatty acid triglyceride adduct with 5 to 20 mol of ethylene oxide,
   (C) 1 to 20% by weight emulsifier that is a partial ester of a polyhydric alcohol and a fatty acid, the partial ester being liquid at 40° C., (D) 10 to 60% by weight water phase comprising a cancer antigen peptide having 8 to 12 amino acids or a dimer thereof, wherein the composition is a W/O emulsion.

11. The cancer vaccine composition of claim 10, comprising
(A') 40 to 60% by weight ester of a fatty acid having 8 to 22 carbon atoms and an alcohol having 2 to 24 carbon atoms, the solidification point of the ester being not more than 10° C.,
(B') 0.5 to 20% by weight nonionic surfactant consisting of a hydroxy fatty acid triglyceride adduct with 5 to 20 mol of ethylene oxide,
(C') 5.0 to 10.0% by weight emulsifier that is a partial ester of a polyhydric alcohol and a fatty acid, the partial ester being liquid at 40° C., and
(D') 30 to 50% by weight water phase comprising a cancer antigen peptide having 8 to 12 amino acids or a dimer thereof.

12. The cancer vaccine composition of claim 10 obtained by diluting 0.25 to 1 part by volume of a water phase comprising a cancer antigen peptide having 8 to 12 amino acids or a dimer thereof with 1 part by volume of an emulsified composition for dilution, wherein the emulsified composition comprises:
(A') 50 to 90% by weight ester of a fatty acid having 8 to 22 carbon atoms and an alcohol having 2 to 24 carbon atoms, the ester having a solidification point of not more than 10° C.,
(B') 0.5 to 20% by weight nonionic surfactant consisting of a hydroxy fatty acid triglyceride adduct with 5 to 20 mol of ethylene oxide,
(C') 1 to 20% by weight emulsifier that is a partial ester of a polyhydric alcohol and a fatty acid, the partial ester being liquid at 40° C., and
(D') 5 to 20% by weight water.

13. A method of inducing a cancer antigen-specific cytotoxic T cell comprising administering to a subject a cancer vaccine composition comprising:
(A) 30 to 80% by weight ester of a fatty acid having 8 to 22 carbon atoms and an alcohol having 2 to 24 carbon atoms, the solidification point of the ester being not more than 10° C.,
(B) 0.5 to 20% by weight nonionic surfactant consisting of a hydroxy fatty acid triglyceride with 5 to 20 mol of ethylene oxide added thereto,
(C) 1 to 20% by weight emulsifier that is a partial ester of a polyhydric alcohol and a fatty acid, the partial ester being liquid at 40° C., and
(D) 10 to 60% by weight water phase comprising a cancer antigen peptide having 8 to 12 amino acids or a dimer thereof,
wherein the composition is a W/O emulsion.

14. The method of claim 13, wherein the composition comprises
(A') 40 to 60% by weight ester of a fatty acid having 8 to 22 carbon atoms and an alcohol having 2 to 24 carbon atoms, the solidification point of the ester being not more than 10° C.,
(B') 0.5 to 20% by weight nonionic surfactant consisting of a hydroxy fatty acid triglyceride adduct with 5 to 20 mol of ethylene oxide,
(C') 5.0 to 10.0% by weight emulsifier that is a partial ester of a polyhydric alcohol and a fatty acid, the partial ester being liquid at 40° C., and
(D') 30 to 50% by weight water phase comprising a cancer antigen peptide having 8 to 12 amino acids or a dimer thereof.

15. The method of claim 13, wherein the cancer vaccine composition is obtained by diluting 0.25 to 1 part by volume of a water phase comprising a cancer antigen peptide having 8 to 12 amino acids or a dimer thereof with 1 part by volume of an emulsified composition for dilution, wherein the emulsified composition comprises:
(A') 50 to 90% by weight ester of a fatty acid having 8 to 22 carbon atoms and an alcohol having 2 to 24 carbon atoms, the ester having a solidification point of not more than 10° C.,
(B') 0.5 to 20% by weight nonionic surfactant consisting of a hydroxy fatty acid triglyceride adduct with 5 to 20 mol of ethylene oxide,
(C') 1 to 20% by weight emulsifier that is a partial ester of a polyhydric alcohol and a fatty acid, the partial ester being liquid at 40° C., and
(D') 5 to 20% by weight water.

16. The method of claim 15, wherein the average particle diameter of the dispersion phase of the emulsified composition for dilution is 50 to 500 nm.

17. A kit for freshly preparing a cancer vaccine composition, comprising a water phase comprising a cancer antigen peptide having 8 to 12 amino acids or a dimer thereof, and an emulsified composition for dilution for diluting the water phase, wherein the emulsified composition for dilution comprises (A) 50 to 90% by weight ester of a fatty acid having 8 to 22 carbon atoms and an alcohol having 2 to 24 carbon atoms, the ester having a solidification point of not more than 10° C., (B) 0.5 to 20% by weight nonionic surfactant consisting of a hydroxy fatty acid triglyceride adduct with 5 to 20 mol of ethylene oxide, (C) 0 to 20% by weight emulsifier that is a partial ester of a polyhydric alcohol and a fatty acid, the partial ester being liquid at 40° C., and (D) 5 to 20% by weight water.

18. An emulsified composition for diluting a cancer antigen peptide having 8 to 12 amino acids or a dimer thereof, consisting essentially of:
(A) 50 to 90% by weight ester of a fatty acid having 8 to 22 carbon atoms and an alcohol having 2 to 24 carbon atoms, the ester having a solidification point of not more than 10° C.,
(B) 0.5 to 20% by weight nonionic surfactant consisting of a hydroxy fatty acid triglyceride adduct with 5 to 20 mol of ethylene oxide,
(C) 0 to 20% by weight emulsifier that is a partial ester of a polyhydric alcohol and a fatty acid, the partial ester being liquid at 40° C., and
(D) 5 to 20% by weight water,
wherein the average particle diameter of the dispersion phase of the emulsified composition for dilution is 50 to 500 nm.

19. An emulsified composition for diluting a cancer antigen peptide having 8 to 12 amino acids or a dimer thereof, consisting of:
(A) 50 to 90% by weight ester of a fatty acid having 8 to 22 carbon atoms and an alcohol having 2 to 24 carbon atoms, the ester having a solidification point of not more than 10° C.,
(B) 0.5 to 20% by weight nonionic surfactant consisting of a hydroxy fatty acid triglyceride adduct with 5 to 20 mol of ethylene oxide,
(C) 0 to 20% by weight emulsifier that is a partial ester of a polyhydric alcohol and a fatty acid, the partial ester being liquid at 40° C., and
(D) 5 to 20% by weight water,
wherein the average particle diameter of the dispersion phase of the emulsified composition for dilution is 50 to 500 nm.

20. A cancer vaccine composition obtained by diluting 0.25 to 1 part by volume of a water phase comprising a cancer antigen peptide having 8 to 12 amino acids or a dimer thereof with 1 part by volume of an emulsified composition for dilution,
wherein the emulsified composition comprises:
(A') 50 to 90% by weight ester of a fatty acid having 8 to 22 carbon atoms and an alcohol having 2 to 24 carbon atoms, the ester having a solidification point of not more than 10° C.,
(B') 0.5 to 20% by weight nonionic surfactant consisting of a hydroxy fatty acid triglyceride adduct with 5 to 20 mol of ethylene oxide,
(C') 0 to 20% by weight emulsifier that is a partial ester of a polyhydric alcohol and a fatty acid, the partial ester being liquid at 40° C., and
(D') 5 to 20% by weight water, and
wherein the average particle diameter of the dispersion phase of the emulsified composition for dilution is 50 to 500 nm.

* * * * *

UNITED STATES PATENT AND TRADEMARK OFFICE
CERTIFICATE OF CORRECTION

PATENT NO. : 8,178,102 B2
APPLICATION NO. : 11/814270
DATED : May 8, 2012
INVENTOR(S) : Koichi Saito et al.

It is certified that error appears in the above-identified patent and that said Letters Patent is hereby corrected as shown below:

In the Specification:

in col. 3, l. 8, change "10° C., at" to --10° C, at-- in col. 3, l. 18, change "10° C., at" to --10° C, at-- in col. 3, l. 24, change "40° C., at" to --40° C, at-- in col. 3, l. 56, change "10° C., at" to --10° C, at-- in col. 3, l. 62, change "40° C., at" to --40° C, at-- in col. 4, l. 10, change "10° C., at" to --10° C, at-- in col. 4, l. 16, change "40° C., at" to --40° C, at-- in col. 5, l. 33, change "10° C., it is" to --10° C, it is-- in col. 7, l. 13, change "40° C. may" to --40° C may-- in col. 12, ll. 3–4, change "5° C., and" to --5° C, and-- in col. 12, l. 4, change "25° C. of" to --25° C of-- in col. 22, l. 23, change "25° C. for" to --25° C for-- in col. 23, Table 14, change "at 5° C. for" to --at 5° C for-- in col. 23, l. 36, change "5° C. for" to --5° C for--

In the Claims:

in col. 39, l. 39, change "than 10° C.," to --than 10° C,-- in col. 39, l. 44, change "40° C., and" to --40° C, and-- in col. 39, l. 52, change "than 10° C.," to --than 10° C,-- in col. 39, l. 58, change "40° C., and" to --40° C, and-- in col. 40, l. 41, change "10° C., (B)" to --10° C, (B)-- in col. 40, l. 46, change "40° C., and" to --40° C, and--

Signed and Sealed this
Twentieth Day of November, 2012

David J. Kappos
*Director of the United States Patent and Trademark Office* in col. 40, l. 61, change "than 10° C.," to --than 10° C,-- in col. 40, l. 67, change "40° C.," to --40° C, and-- in col. 41, l. 10, change "than 10° C.," to --than 10° C,-- in col. 41, l. 15, change "40° C., and" to --40° C, and-- in col. 41, l. 27, change "10° C.," to --10° C,-- in col. 41, l. 33, change "40° C., and" to --40° C, and-- in col. 41, l. 40, change "10° C.," to --10° C,-- in col. 41, l. 46, change "40° C., and" to --40° C, and-- in col. 41, l. 56, change "than 10° C.," to --than 10° C,-- in col. 41, l. 61, change "40° C., and" to --40° C, and-- in col. 42, l. 7, change "than 10° C.," to --than 10° C,-- in col. 42, l. 14, change "40° C., and" to --40° C, and-- in col. 42, l. 27, change "10° C., (B)" to --10° C, (B)-- in col. 42, l. 31, change "40° C., and" to --40° C, and-- in col. 42, l. 39, change "than 10° C.," to --than 10° C,-- in col. 42, l. 45, change "40° C., and" to --40° C, and-- in col. 42, l. 56, change "than 10° C.," to --than 10° C,-- in col. 42, l. 63, change "40° C., and" to --40° C, and-- in col. 43, l. 9, change "than 10° C.," to --than 10° C,-- in col. 44, l. 3, change "40° C., and" to --40° C, and--

UNITED STATES PATENT AND TRADEMARK OFFICE
CERTIFICATE OF CORRECTION

PATENT NO. : 8,178,102 B2
APPLICATION NO. : 11/814270
DATED : May 15, 2012
INVENTOR(S) : Koichi Saito et al.

It is certified that error appears in the above-identified patent and that said Letters Patent is hereby corrected as shown below:

In the Specification:

in col. 3, l. 8, change "10° C., at" to --10° C, at-- in col. 3, l. 18, change "10° C., at" to --10° C, at-- in col. 3, l. 24, change "40° C., at" to --40° C, at-- in col. 3, l. 56, change "10° C., at" to --10° C, at-- in col. 3, l. 62, change "40° C., at" to --40° C, at-- in col. 4, l. 10, change "10° C., at" to --10° C, at-- in col. 4, l. 16, change "40° C., at" to --40° C, at-- in col. 5, l. 33, change "10° C., it is" to --10° C, it is-- in col. 7, l. 13, change "40° C. may" to --40° C may-- in col. 12, ll. 3-4, change "5° C., and" to --5° C, and-- in col. 12, l. 4, change "25° C. of" to --25° C of-- in col. 22, l. 23, change "25° C. for" to --25° C for-- in col. 23, Table 14, change "at 5° C. for" to --at 5° C for-- in col. 23, l. 36, change "5° C. for" to --5° C for--

In the Claims:

in col. 39, l. 39, change "than 10° C.," to --than 10° C,-- in col. 39, l. 44, change "40° C., and" to --40° C, and-- in col. 39, l. 52, change "than 10° C.," to --than 10° C,--

This certificate supersedes the Certificate of Correction issued November 20, 2012.

Signed and Sealed this
Twenty-first Day of May, 2013

Teresa Stanek Rea
*Acting Director of the United States Patent and Trademark Office*

CERTIFICATE OF CORRECTION (continued)
U.S. Pat. No. 8,178,102 B2 in col. 39, l. 58, change "40° C., and" to --40° C, and-- in col. 40, l. 41, change "10° C., (B)" to --10° C, (B)-- in col. 40, l. 46, change "40° C., and" to --40° C, and-- in col. 40, l. 61, change "than 10° C.," to --than 10° C,-- in col. 40, l. 67, change "40° C.," to --40° C, and-- in col. 41, l. 10, change "than 10° C.," to --than 10° C,-- in col. 41, l. 15, change "40° C., and" to --40° C, and-- in col. 41, l. 27, change "10° C.," to --10° C,-- in col. 41, l. 33, change "40° C., and" to --40° C, and-- in col. 41, l. 40, change "10° C.," to --10° C,-- in col. 41, l. 46, change "40° C., and" to --40° C, and-- in col. 41, l. 56, change "than 10° C.," to --than 10° C,-- in col. 41, l. 61, change "40° C., and" to --40° C, and-- in col. 42, l. 7, change "than 10° C.," to --than 10° C,-- in col. 42, l. 14, change "40° C., and" to --40° C, and-- in col. 42, l. 27, change "10° C., (B)" to --10° C, (B)-- in col. 42, l. 31, change "40° C., and" to --40° C, and-- in col. 42, l. 39, change "than 10° C.," to --than 10° C,-- in col. 42, l. 45, change "40° C., and" to --40° C, and-- in col. 42, l. 56, change "than 10° C.," to --than 10° C,-- in col. 42, l. 63, change "40° C., and" to --40° C, and-- in col. 43, l. 9, change "than 10° C.," to --than 10° C,-- in col. 44, l. 3, change "40° C., and" to --40° C, and--

SEQUENCE LISTING

```
<160> NUMBER OF SEQ ID NOS: 53

<210> SEQ ID NO 1
<211> LENGTH: 9
<212> TYPE: PRT
<213> ORGANISM: Homo sapiens

<400> SEQUENCE: 1

Lys Thr Trp Gly Gln Tyr Trp Gln Val
1               5

<210> SEQ ID NO 2
<211> LENGTH: 10
<212> TYPE: PRT
<213> ORGANISM: Homo sapiens

<400> SEQUENCE: 2

Ala Met Leu Gly Thr His Thr Met Glu Val
1               5                   10

<210> SEQ ID NO 3
<211> LENGTH: 9
<212> TYPE: PRT
<213> ORGANISM: Homo sapiens

<400> SEQUENCE: 3

Met Leu Gly Thr His Thr Met Glu Val
1               5

<210> SEQ ID NO 4
<211> LENGTH: 9
<212> TYPE: PRT
<213> ORGANISM: Homo sapiens

<400> SEQUENCE: 4

Ile Thr Asp Gln Val Pro Phe Ser Val
1               5

<210> SEQ ID NO 5
<211> LENGTH: 9
<212> TYPE: PRT
<213> ORGANISM: Homo sapiens

<400> SEQUENCE: 5

Tyr Leu Glu Pro Gly Pro Val Thr Ala
1               5

<210> SEQ ID NO 6
<211> LENGTH: 10
<212> TYPE: PRT
<213> ORGANISM: Homo sapiens

<400> SEQUENCE: 6

Leu Leu Asp Gly Thr Ala Thr Leu Arg Leu
1               5                   10

<210> SEQ ID NO 7
<211> LENGTH: 10
```

```
<212> TYPE: PRT
<213> ORGANISM: Homo sapiens

<400> SEQUENCE: 7

Val Leu Tyr Arg Tyr Gly Ser Phe Ser Val
1               5                   10

<210> SEQ ID NO 8
<211> LENGTH: 10
<212> TYPE: PRT
<213> ORGANISM: Homo sapiens

<400> SEQUENCE: 8

Ser Leu Ala Asp Thr Asn Ser Leu Ala Val
1               5                   10

<210> SEQ ID NO 9
<211> LENGTH: 9
<212> TYPE: PRT
<213> ORGANISM: Homo sapiens

<400> SEQUENCE: 9

Arg Leu Met Lys Gln Asp Phe Ser Val
1               5

<210> SEQ ID NO 10
<211> LENGTH: 9
<212> TYPE: PRT
<213> ORGANISM: Homo sapiens

<400> SEQUENCE: 10

Arg Leu Pro Arg Ile Phe Cys Ser Cys
1               5

<210> SEQ ID NO 11
<211> LENGTH: 9
<212> TYPE: PRT
<213> ORGANISM: Homo sapiens

<400> SEQUENCE: 11

Val Tyr Phe Phe Leu Pro Asp His Leu
1               5

<210> SEQ ID NO 12
<211> LENGTH: 9
<212> TYPE: PRT
<213> ORGANISM: Homo sapiens

<400> SEQUENCE: 12

Ala Ala Gly Ile Gly Ile Leu Thr Val
1               5

<210> SEQ ID NO 13
<211> LENGTH: 10
<212> TYPE: PRT
<213> ORGANISM: Homo sapiens

<400> SEQUENCE: 13

Glu Ala Ala Gly Ile Gly Ile Leu Thr Val
1               5                   10

<210> SEQ ID NO 14
<211> LENGTH: 9
<212> TYPE: PRT
<213> ORGANISM: Homo sapiens
```

```
<400> SEQUENCE: 14

Ile Leu Thr Val Ile Leu Gly Val Leu
1               5

<210> SEQ ID NO 15
<211> LENGTH: 9
<212> TYPE: PRT
<213> ORGANISM: Homo sapiens

<400> SEQUENCE: 15

Met Leu Leu Ala Val Leu Tyr Cys Leu
1               5

<210> SEQ ID NO 16
<211> LENGTH: 9
<212> TYPE: PRT
<213> ORGANISM: Homo sapiens

<400> SEQUENCE: 16

Tyr Met Asp Gly Thr Met Ser Gln Val
1               5

<210> SEQ ID NO 17
<211> LENGTH: 9
<212> TYPE: PRT
<213> ORGANISM: Homo sapiens

<400> SEQUENCE: 17

Ala Phe Leu Pro Trp His Arg Leu Phe
1               5

<210> SEQ ID NO 18
<211> LENGTH: 10
<212> TYPE: PRT
<213> ORGANISM: Homo sapiens

<400> SEQUENCE: 18

Ala Phe Leu Pro Trp His Arg Leu Phe Leu
1               5                   10

<210> SEQ ID NO 19
<211> LENGTH: 9
<212> TYPE: PRT
<213> ORGANISM: Homo sapiens

<400> SEQUENCE: 19

Tyr Leu Ser Gly Ala Asn Leu Asn Leu
1               5

<210> SEQ ID NO 20
<211> LENGTH: 9
<212> TYPE: PRT
<213> ORGANISM: Homo sapiens

<400> SEQUENCE: 20

Ile Met Ile Gly Val Leu Val Gly Val
1               5

<210> SEQ ID NO 21
<211> LENGTH: 9
<212> TYPE: PRT
<213> ORGANISM: Homo sapiens

<400> SEQUENCE: 21

Leu Leu Thr Phe Trp Asn Pro Pro Thr
```

```
                                1               5

<210> SEQ ID NO 22
<211> LENGTH: 10
<212> TYPE: PRT
<213> ORGANISM: Homo sapiens

<400> SEQUENCE: 22

Gln Tyr Ser Trp Phe Val Asn Gly Thr Phe
  1               5                  10

<210> SEQ ID NO 23
<211> LENGTH: 9
<212> TYPE: PRT
<213> ORGANISM: Homo sapiens

<400> SEQUENCE: 23

Thr Tyr Ala Cys Phe Val Ser Asn Leu
  1               5

<210> SEQ ID NO 24
<211> LENGTH: 10
<212> TYPE: PRT
<213> ORGANISM: Homo sapiens

<400> SEQUENCE: 24

Phe Leu Thr Pro Lys Lys Leu Gln Cys Val
  1               5                  10

<210> SEQ ID NO 25
<211> LENGTH: 10
<212> TYPE: PRT
<213> ORGANISM: Homo sapiens

<400> SEQUENCE: 25

Val Ser His Ser Phe Pro His Pro Leu Tyr
  1               5                  10

<210> SEQ ID NO 26
<211> LENGTH: 10
<212> TYPE: PRT
<213> ORGANISM: Homo sapiens

<400> SEQUENCE: 26

Val Ile Ser Asn Asp Val Cys Ala Gln Val
  1               5                  10

<210> SEQ ID NO 27
<211> LENGTH: 9
<212> TYPE: PRT
<213> ORGANISM: Homo sapiens

<400> SEQUENCE: 27

Cys Tyr Ala Ser Gly Trp Gly Ser Ile
  1               5

<210> SEQ ID NO 28
<211> LENGTH: 9
<212> TYPE: PRT
<213> ORGANISM: Homo sapiens

<400> SEQUENCE: 28

Ser Thr Ala Pro Pro Val His Asn Val
  1               5
```

```
<210> SEQ ID NO 29
<211> LENGTH: 10
<212> TYPE: PRT
<213> ORGANISM: Homo sapiens

<400> SEQUENCE: 29

Gln Ile Ile Ser Ala Val Val Gly Ile Leu
1               5                   10

<210> SEQ ID NO 30
<211> LENGTH: 9
<212> TYPE: PRT
<213> ORGANISM: Homo sapiens

<400> SEQUENCE: 30

Gln Leu Phe Glu Asp Asn Tyr Ala Leu
1               5

<210> SEQ ID NO 31
<211> LENGTH: 9
<212> TYPE: PRT
<213> ORGANISM: Homo sapiens

<400> SEQUENCE: 31

Lys Ile Phe Gly Ser Leu Ala Phe Leu
1               5

<210> SEQ ID NO 32
<211> LENGTH: 8
<212> TYPE: PRT
<213> ORGANISM: Homo sapiens

<400> SEQUENCE: 32

Cys Leu Thr Ser Val Gln Leu Val
1               5

<210> SEQ ID NO 33
<211> LENGTH: 10
<212> TYPE: PRT
<213> ORGANISM: Homo sapiens

<400> SEQUENCE: 33

Val Met Ala Gly Val Gly Ser Pro Tyr Val
1               5                   10

<210> SEQ ID NO 34
<211> LENGTH: 9
<212> TYPE: PRT
<213> ORGANISM: Homo sapiens

<400> SEQUENCE: 34

Arg Leu Leu Gln Glu Thr Glu Leu Val
1               5

<210> SEQ ID NO 35
<211> LENGTH: 9
<212> TYPE: PRT
<213> ORGANISM: Homo sapiens

<400> SEQUENCE: 35

Pro Tyr Val Ser Arg Leu Leu Gly Ile
1               5

<210> SEQ ID NO 36
<211> LENGTH: 9
<212> TYPE: PRT
```

```
<213> ORGANISM: Homo sapiens

<400> SEQUENCE: 36

Thr Tyr Leu Pro Thr Asn Ala Ser Leu
1               5

<210> SEQ ID NO 37
<211> LENGTH: 9
<212> TYPE: PRT
<213> ORGANISM: Homo sapiens

<400> SEQUENCE: 37

Asn Tyr Lys His Cys Phe Pro Glu Ile
1               5

<210> SEQ ID NO 38
<211> LENGTH: 9
<212> TYPE: PRT
<213> ORGANISM: Homo sapiens

<400> SEQUENCE: 38

Phe Leu Trp Gly Pro Arg Ala Leu Val
1               5

<210> SEQ ID NO 39
<211> LENGTH: 9
<212> TYPE: PRT
<213> ORGANISM: Homo sapiens

<400> SEQUENCE: 39

Lys Val Ala Glu Leu Val His Phe Leu
1               5

<210> SEQ ID NO 40
<211> LENGTH: 9
<212> TYPE: PRT
<213> ORGANISM: Homo sapiens

<400> SEQUENCE: 40

Ile Met Pro Lys Ala Gly Leu Leu Ile
1               5

<210> SEQ ID NO 41
<211> LENGTH: 9
<212> TYPE: PRT
<213> ORGANISM: Homo sapiens

<400> SEQUENCE: 41

Thr Phe Pro Asp Leu Glu Ser Glu Phe
1               5

<210> SEQ ID NO 42
<211> LENGTH: 9
<212> TYPE: PRT
<213> ORGANISM: Homo sapiens

<400> SEQUENCE: 42

Ser Leu Leu Met Trp Ile Thr Gln Cys
1               5

<210> SEQ ID NO 43
<211> LENGTH: 11
<212> TYPE: PRT
<213> ORGANISM: Homo sapiens

<400> SEQUENCE: 43
```

-continued

Ser Leu Leu Met Trp Ile Thr Gln Cys Phe Leu
1               5                   10

<210> SEQ ID NO 44
<211> LENGTH: 9
<212> TYPE: PRT
<213> ORGANISM: Homo sapiens

<400> SEQUENCE: 44

Gln Leu Ser Leu Leu Met Trp Ile Thr
1               5

<210> SEQ ID NO 45
<211> LENGTH: 9
<212> TYPE: PRT
<213> ORGANISM: Homo sapiens

<400> SEQUENCE: 45

Glu Tyr Arg Gly Phe Thr Gln Asp Phe
1               5

<210> SEQ ID NO 46
<211> LENGTH: 10
<212> TYPE: PRT
<213> ORGANISM: Homo sapiens

<400> SEQUENCE: 46

Val Tyr Asp Tyr Asn Cys His Val Asp Leu
1               5                   10

<210> SEQ ID NO 47
<211> LENGTH: 9
<212> TYPE: PRT
<213> ORGANISM: Homo sapiens

<400> SEQUENCE: 47

Ile Leu Ala Lys Phe Leu His Trp Leu
1               5

<210> SEQ ID NO 48
<211> LENGTH: 9
<212> TYPE: PRT
<213> ORGANISM: Homo sapiens

<400> SEQUENCE: 48

Val Tyr Ala Glu Thr Lys His Phe Leu
1               5

<210> SEQ ID NO 49
<211> LENGTH: 9
<212> TYPE: PRT
<213> ORGANISM: Homo sapiens

<400> SEQUENCE: 49

Val Tyr Gly Phe Val Arg Ala Cys Leu
1               5

<210> SEQ ID NO 50
<211> LENGTH: 9
<212> TYPE: PRT
<213> ORGANISM: Homo sapiens

<400> SEQUENCE: 50

Arg Met Phe Pro Asn Ala Pro Tyr Leu
1               5

```
<210> SEQ ID NO 51
<211> LENGTH: 9
<212> TYPE: PRT
<213> ORGANISM: Homo sapiens

<400> SEQUENCE: 51

Cys Met Thr Trp Asn Gln Met Asn Leu
1               5

<210> SEQ ID NO 52
<211> LENGTH: 9
<212> TYPE: PRT
<213> ORGANISM: Homo sapiens

<400> SEQUENCE: 52

Arg Trp Pro Ser Cys Gln Lys Lys Phe
1               5

<210> SEQ ID NO 53
<211> LENGTH: 9
<212> TYPE: PRT
<213> ORGANISM: Homo sapiens

<400> SEQUENCE: 53

Ala Tyr Ala Cys Asn Thr Ser Thr Leu
1               5
```